(12) United States Patent
Forsell

(10) Patent No.: US 12,048,629 B1
(45) Date of Patent: *Jul. 30, 2024

(54) HIP JOINT DEVICE

(71) Applicant: Peter Forsell, Lund (SE)

(72) Inventor: Peter Forsell, Lund (SE)

( * ) Notice: Subject to any disclaimer, the term of this patent is extended or adjusted under 35 U.S.C. 154(b) by 572 days.

This patent is subject to a terminal disclaimer.

(21) Appl. No.: 17/130,055

(22) Filed: Dec. 22, 2020

Related U.S. Application Data

(63) Continuation of application No. 15/713,676, filed on Sep. 24, 2017, now Pat. No. 10,898,334, which is a (Continued)

(30) Foreign Application Priority Data

| Jul. 10, 2009 | (SE) | 0900957-2 |
|---|---|---|
| Jul. 10, 2009 | (SE) | 0900958-0 |
| Jul. 10, 2009 | (SE) | 0900959-8 |
| Jul. 10, 2009 | (SE) | 0900960-6 |
| Jul. 10, 2009 | (SE) | 0900962-2 |
| Jul. 10, 2009 | (SE) | 0900963-0 |
| Jul. 10, 2009 | (SE) | 0900965-5 |
| Jul. 10, 2009 | (SE) | 0900966-3 |
| Jul. 10, 2009 | (SE) | 0900968-9 |
| Jul. 10, 2009 | (SE) | 0900969-7 |
| Jul. 10, 2009 | (SE) | 0900970-5 |
| Jul. 10, 2009 | (SE) | 0900972-1 |
| Jul. 10, 2009 | (SE) | 0900973-9 |
| Jul. 10, 2009 | (SE) | 0900974-7 |
| Jul. 10, 2009 | (SE) | 0900976-2 |
| Jul. 10, 2009 | (SE) | 0900978-8 |
| Jul. 10, 2009 | (SE) | 0900981-2 |

(51) Int. Cl.
| A61F 2/36 | (2006.01) |
|---|---|
| A61F 2/28 | (2006.01) |
| A61F 2/30 | (2006.01) |

(52) U.S. Cl.
CPC .......... *A61F 2/3603* (2013.01); *A61F 2/2814* (2013.01); *A61F 2002/2828* (2013.01); *A61F 2002/30462* (2013.01); *A61F 2002/30469* (2013.01); *A61F 2002/30471* (2013.01); *A61F 2002/30495* (2013.01); *A61F 2002/305* (2013.01); *A61F 2002/30545* (2013.01); *A61F 2002/30593* (2013.01); *A61F 2002/30594* (2013.01);
(Continued)

(58) Field of Classification Search
CPC .............................. A61F 2/3603; A61F 2/2814
See application file for complete search history.

(56) References Cited

U.S. PATENT DOCUMENTS

| 8,632,602 B2 * | 1/2014 | Vlachos | A61F 2/3603 |
| | | | 623/23.14 |
| 2009/0192620 A1 * | 7/2009 | Ebbitt | A61F 2/4607 |
| | | | 623/18.11 |

* cited by examiner

*Primary Examiner* — Brian A Dukert

(57) ABSTRACT

A method for implantation of a locking member in a hip joint of a patient is disclosed. The method comprises; performing an operation in a hip joint surgically or arthroscopically, placing an artificial hollow caput femur surface mounted onto caput femur, placing a locking member for assisting in the fixation of the artificial caput femur surface with at least one extending portion adapted to clasp a portion of the caput and/or collum femur. The locking member comprises an element locking the artificial caput femur surface such that the caput femur remains clasped and restrained in said artificial caput femur surface.

9 Claims, 14 Drawing Sheets

Related U.S. Application Data continuation of application No. 13/382,656, filed as application No. PCT/SE2010/000192 on Jul. 12, 2010, now Pat. No. 9,770,336.

(60) Provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009, provisional application No. 61/229,738, filed on Jul. 30, 2009, provisional application No. 61/229,739, filed on Jul. 30, 2009, provisional application No. 61/229,743, filed on Jul. 30, 2009, provisional application No. 61/229,745, filed on Jul. 30, 2009.

(52) U.S. Cl.
CPC ............... *A61F 2002/30616* (2013.01); *A61F 2002/30757* (2013.01); *A61F 2002/30818* (2013.01); *A61F 2/3601* (2013.01); *A61F 2002/3615* (2013.01); *A61F 2220/0025* (2013.01)

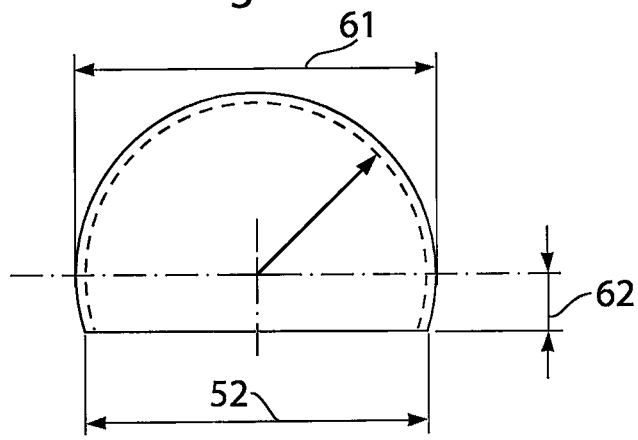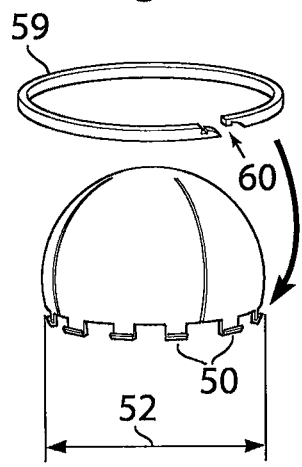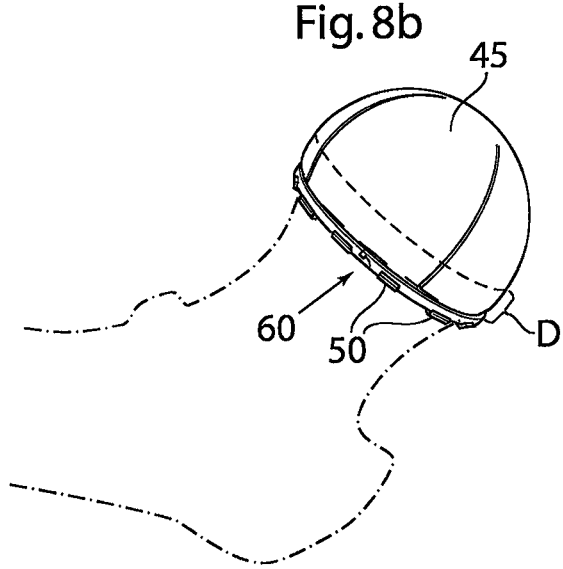

Fig. 9
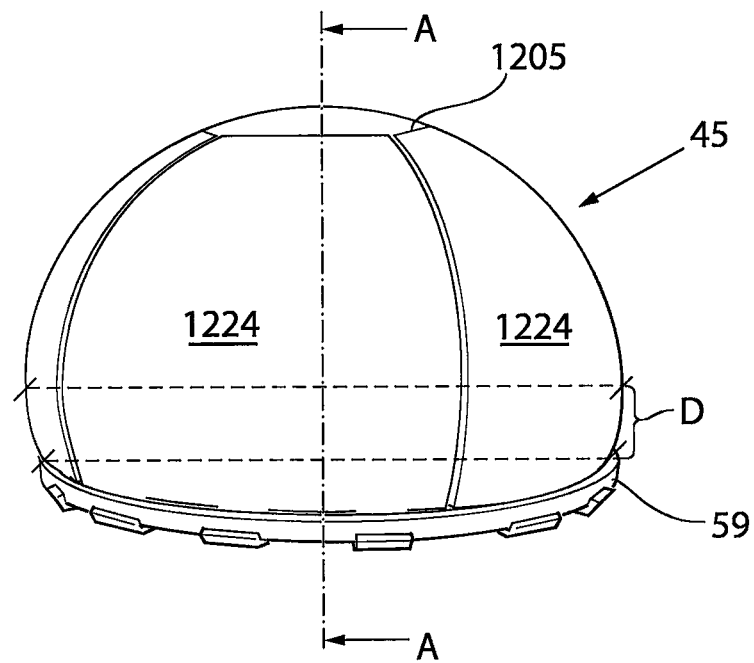
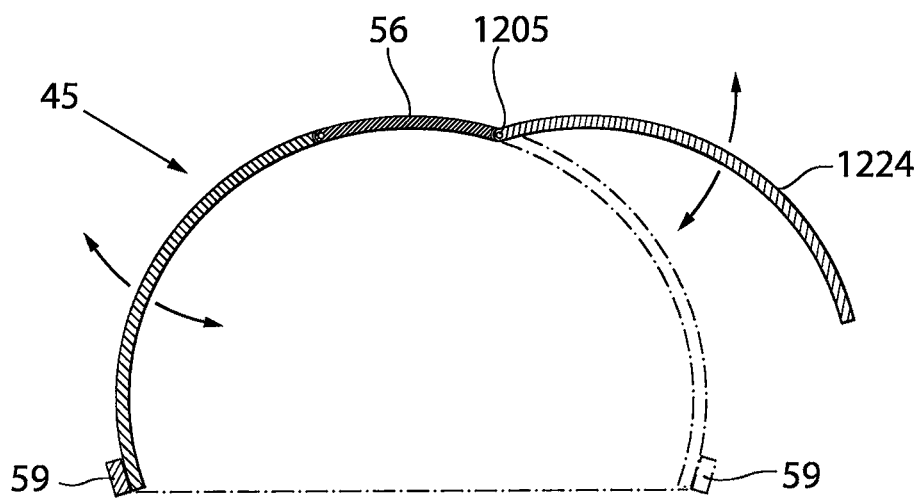
A-A

Fig.13a
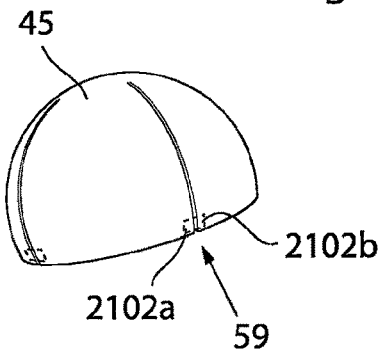
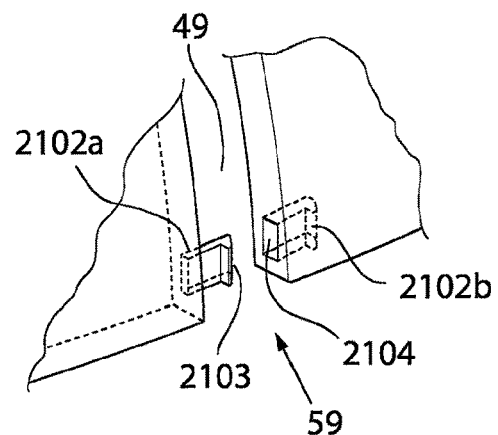
Fig.13b
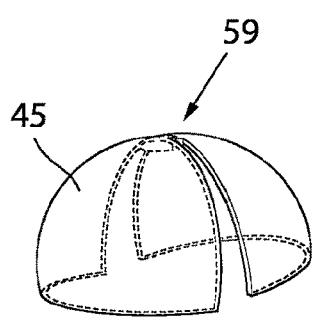
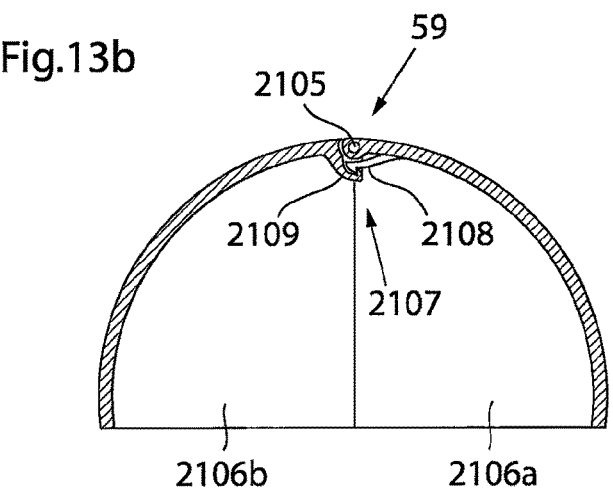
Fig.14
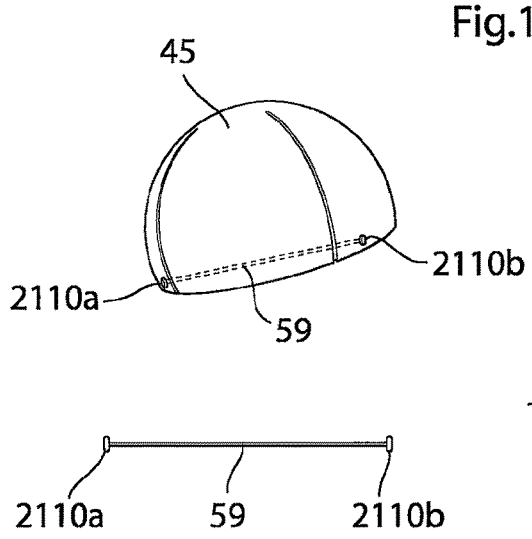
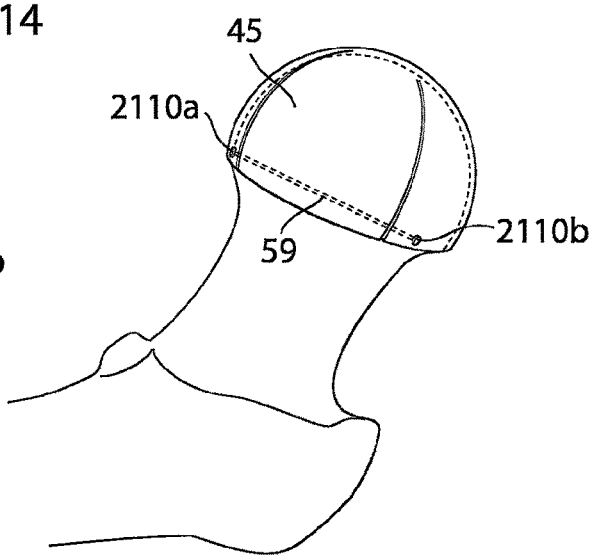

HIP JOINT DEVICE

This application is a continuation of U.S. application Ser. No. 15/713,676, filed Sep. 9, 2017, which is a continuation of U.S. application Ser. No. 13/382,656, filed Jan. 6, 2012, which is the U.S. national phase of International Application No. PCT/SE10/00192, filed Jul. 12, 2010, which designated the U.S. and claims the benefit of U.S. Provisional Application Nos. 61/229,739, 61/229,743, 61/229,745, 61/229,746, 61/229,747, 61/229,748, 61/229,751, 61/229,752, 61/229,755, 61/229,761, 61/229,767, 61/229,778, 61/229,786, 61/229,789, 61/229,796, 61/229,735 and 61/229,738, all filed on Jul. 30, 2009 and priority from Swedish patent application nos. 0900958-0, 0900978-8, 0900976-2, 0900974-7, 0900973-9, 0900972-1, 0900970-5, 0900969-7, 0900968-9, 0900966-3, 0900965-5, 0900963-0, 0900962-2, 0900960-6, 0900959-8, 0900957-2 and 0900981-2, all filed Jul. 10, 2009, the entire contents of each of which are hereby incorporated by reference in this application.

TECHNICAL FIELD

The present invention relates generally to medical devices for implantation in a hip joint.

BACKGROUND ART

The hip joint is a synovial joint, joining the pelvis to the proximal portion of the femoral bone. Synovial joints are the most common types of joints in mammals, and are typical of nearly all limb joints. The contacting surfaces of said the pelvic, the acetabulum, and the contacting surface of the femoral bone, the caput femur, are smooth and rounded, and covered by articular cartilage. A synovial membrane, encapsulates the joint, forming a hip joint cavity, which contains synovial fluid. Outside the synovial membrane is a fibrous capsule and ligaments, forming an articular capsule.

There are both natural and pathological processes leading to deteriorated joint function. With age and wear, the articular cartilage becomes less effective as a shock absorber and a lubricated surface. Different degenerative joint diseases, such as arthritis, osteoartrithis, or osteoarthrosis, accelerate the deterioration.

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through an incision in the hip and upper thigh and through Fascia Lata and the lateral muscles of the thigh. To get access to the joint, the supporting Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The complications after hip joint surgery includes dislocation of the hip joint and loosening of the prosthesis from its fixation in the femoral bone. The loosening and/or dislocation of the prosthesis could be induced by an abnormal strain being placed on the hip joint from e.g. the patient falling or making a rapid movement of the hip, or by a bodily macrophage reaction.

SUMMARY

A locking member for implantation in a hip joint of a patient is provided. The locking member is adapted to fixate a medical device comprising an artificial hollow caput femur surface to a caput femur hip joint surface. The locking member comprises a loop-shaped element with a first and a second end adapted be mechanically connected using an engagement member, so that it forms a closed loop-shaped element with a circumference encircling the caput femur or collum femur.

According to one embodiment, the loop-shaped element is adapted to be connected in at least a first and second locking position. The loop-shaped element could have a first inner circumference, when the loop-shaped element is connected in the first locking position, the loop shaped element has a second smaller inner circumference, when the loop shaped element is connected in the second locking position. This way the locking member could be adapted for the particular patient.

According to another embodiment the loop-shaped element is further adapted to be connected in a third locking position. The loop-shaped element has a third inner circumference, when connected in the third locking position, being smaller than the first and second inner circumference.

According to yet another embodiment, the locking member could further be adapted to be arranged in an area extending a distance beyond the maximum diameter of the caput femur.

The engagement member could according to one embodiment comprise a first and a second engagement member part arranged at said first and second locking member end, respectively.

The first and second engagement member could be adapted to mechanically self connect by introducing the first engagement member into the second engagement member. According to one embodiment the first and second engagement member parts could have the shape of protrusions extending from the first and second locking member ends. The first and second engagement member could extend axially from the first and second locking member ends to form a horizontally arranged gripping claw.

According to yet another embodiment, the first and second engagement member extends radially from the first and second locking member ends, to form a vertically arranged gripping claw.

The locking member, according to any of the embodiments, could comprises a first engagement member part having the shape of a protrusion extending from the first locking member end and said second engagement member part has the form of at least one recess or hole.

According to yet another embodiment the first and second ends of the locking member could be connected by using an engagement member comprising two pivotable locking parts.

According to yet another embodiment, the first locking part could be pivotably attached both to the first end of the locking member and to the second locking part.

The second locking part could, according to one embodiment be attached to the first locking part in an engagement point arranged between the outer ends of the first locking part.

According to yet another embodiment the second locking part could be attached to the first locking part in a point arranged substantially in the middle of said the locking part.

According to yet another embodiment, the second locking part could be adapted to engage with a protruding part arranged in the second end of the locking member.

The first and second locking member ends could be adapted to be pulled together by pivoting the first locking part around its engagement point in the first end of the locking member.

According to yet another embodiment, the first and second locking member ends could be arranged overlapping each other when locked together.

According to yet another embodiment the first and second locking member ends are arranged end to end when locked together.

A medical device system for implantation in a hip joint of a patient is further provided. The hip joint has a caput femur hip joint surface partly being the contacting surface of the hip joint, the hip joint further having a collum femur, having a first axial distribution leading to a caput femur. A center axis of the first axial distribution of the collum femur and the caput femur is the caput femur center axis, and the collum femur is placed more distal than caput femur. The medical device comprises: an artificial caput femur surface being hollow, having a major opening adapted to be directed towards the caput femur or a surgically modified caput femur. The artificial caput femur surface is adapted to replace a caput femur hip joint surface. The artificial caput femur surface further has a medical device caput center axis passing through the major opening, being aligned with the caput femur center axis, when the medical device is implanted in a functional position in the hip joint. The medical device comprises a central part and a surrounding part, the central part being aligned with the medical device center axis and the surrounding part surrounding the surface of the caput femur or the surgically modified caput femur, not including the central part. The medical device further comprises an inner surface adapted to have a first distal distance extending perpendicularly from the medical device caput center axis to the inner surface of the surrounding part of the artificial caput femur surface. The first distal distance is shorter than a second proximal distance extending perpendicularly from the medical device caput center axis to the inner surface of the artificial caput femur surface, the second proximal distance extends from a more proximal position on the medical device caput center axis than the first distal distance, being the second proximal distance, when the artificial caput femur surface is implanted in the functional position in the hip joint. The medical device system further comprises a locking member adapted to fixate the medical device to the caput femur, the locking member comprises a loop-shaped element with a first and a second end adapted be mechanically connected using an engagement member so that it forms a closed loop-shaped element with a circumference encircling the caput femur or collum femur. The hollow artificial caput femur surface could be adapted to at least partly cover the caput femur or at least partly cover a surgically modified caput femur, when implanted in a functional position in the hip joint.

According to yet another embodiment the artificial caput femur surface could be adapted to be placed in an acetabulum bowl, or an artificial replacement therefore, when implanted in the functional position in the hip joint.

According to yet another embodiment the artificial caput femur surface could be adapted to have a changeable first distal distance, thus adapted to be mounted onto the caput femur or surgically modified caput femur, when implanted in the hip joint.

The artificial caput femur surface could according to another embodiment, be adapted to have the maximum second proximal distance, extending perpendicularly from the medical device caput center axis to the inner surface of the artificial caput femur surface, wherein the maximum second proximal distance could be located on a part of the medical device caput center axis located more proximal than the major opening, when the artificial caput femur surface is mounted in the functional position in the hip joint, wherein the artificial caput femur surface is adapted to have the closest first distal distance extending perpendicularly from the medical device caput center axis to the inner surface of the artificial caput femur surface, could be smaller than the maximum second proximal distance, wherein the maximum second proximal distance could be extending from the medical device caput center axis more proximal than the closest first distal distance, when implanted in the functional position in the hip joint.

According to yet another embodiment the caput femur has a substantially ball shaped configuration with an outer maximum radius perpendicular to the caput femur center axis, the caput femur being placed in a bowl shaped acetabulum, having a major opening, the caput femur and the acetabulum having one hip joint surface each, placed towards and contacting each other, the hip joint surfaces carrying weight in the hip joint, wherein the caput femur could be placed more proximal than the collum femur and the caput femur could be placed more distal than the acetabulum, wherein the medical device could comprise a central part and a surrounding part, the central part being aligned with the medical device caput center axis and the surrounding part surrounding the surface of the caput femur or partly surgically modified caput femur surface not including the central part, wherein the caput femur or an artificial caput femur surface, could have a maximum caput femur radius cross-section, in which the outer maximum radius of the caput femur or the artificial caput femur surface could be forming a circular extending maximum caput femur or artificial caput femur radius circle, extending perpendicular to the caput femur center axis, defining the maximum caput femur radius cross-section perpendicular to the caput femur center axis or perpendicular to the aligned medical device caput center axis, when the artificial caput femur surface is placed in said functional position, wherein the surrounding part of at least one artificial caput femur surface could comprise at least one first beyond part for extending in distal direction at least partly beyond the maximum artificial caput femur surface radius cross-section, when the artificial caput femur surface is placed in the functional position, when the artificial caput femur surface is implanted in the hip joint, wherein at least one first beyond part could be adapted to have a closest perpendicular distance to the medical device caput center axis, being smaller than an inner maximum distance, extending perpendicularly from the artificial medical device caput enter axis to the inner surface of the artificial caput femur surface, when the artificial caput femur surface is placed in a functional position in the hip joint, thus adapted to create a more stable position of the artificial caput femur surface when mounted in the hip joint.

In accordance to yet another embodiment the maximum inner distance could be extending from one or more pre-defined points selected along a lengthwise extending part of the medical device caput center axis, in which the lengthwise extending part is defined by; two cross-sections of the artificial caput femur surface, extending perpendicular to the medical device caput center axis, from both the distal and proximal end points of the part of said medical device caput center axis, in which both cross-sections are placed at the outer limit of the weight carrying surface of the artificial caput femur surface, in proximal and distal direction, respectively, wherein the part of the medical device caput center axis is placed between the cross-sections, the maximum inner distance could be extending from the medical device caput center axis proximal to the major opening, wherein the lengthwise extending part of the medical device caput center axis could be placed more proximal than the major opening, when the artificial caput femur surface is mounted in the functional position in the hip joint.

According to yet another embodiment a first distal distance could be defined in a first position, defined by the position in distal/proximal direction the medical device caput center axis, and an rotating angle perpendicular to the medical device caput center axis, in which the first distal distance could be extending from the medical device caput center axis, where the first distal distance in the first distal distance position has a first value, wherein the artificial caput femur surface could be adapted to be rotatable from a first rotation position onto the caput femur or a surgically modified caput femur and wherein the inner surface is adapted to have a shape allowing a change of the first distal distance in the first distal distance position, when the artificial caput femur surface has been rotated to a second rotating position, wherein the first distal distance in the first distal position in the second rotation position has a second value, and wherein the second value could be smaller than the first value, when the artificial caput femur surface is mounted onto the caput femur or surgically modified caput femur, when implanted in the hip joint.

According to yet another embodiment the medical device could further be adapted to: have a diameter of the major opening of the hollow artificial caput femur surface, larger than the diameter of the caput femur or a surgical modified caput femur, when introduced onto the caput femur, and have a diameter of the major opening of the hollow artificial caput femur surface, smaller than the diameter of the caput femur or a surgical modified caput femur, after mounting of the artificial caput femur surface on the caput femur in the functional position thereon.

The medical device, in yet another embodiment, could further comprises at least one slit in the artificial caput femur surface allowing the device to vary the diameter of the major opening, thus allowing the device to be mounted on the caput femur.

According to yet another embodiment the major opening could have, at least partly, a diameter or cross sectional distance adapted to be changed in at least one of the following ways: increase to be able to mount the medical device on the caput femur, decrease to mechanically fixate and enable a stable position of the medical device on the caput femur when mounted thereon.

According to yet another embodiment the closest distance from the inner surface of the first beyond part to the medical device caput center axis, perpendicular to the medical device caput center axis, could be adapted to be adjustable, for allowing the diameter of the major opening to be changed. The closest distance from the inner surface of the first beyond part to the medical device caput center axis, perpendicular to the medical device caput center axis, could be adapted to be adjustable by the beyond part comprising at least one of the elements selected from a list consisting of: an elastic portion, a bendable portion, a flexible portion, a compressible portion, and a movable portion.

According to yet another embodiment the closest distance from the inner surface of the first beyond part to the medical device caput center axis, perpendicular to the medical device caput center axis, could be adapted to be adjusted by the locking member.

According to yet another embodiment the medical device could comprise at least two parts adapted to be connected to each other during a surgical or arthroscopic/laparoscopic procedure.

The artificial caput femur surface, in yet another embodiment, could be incomplete in its surface distribution.

According to yet another embodiment the at least two surface parts could be adapted to be mechanically connected to each other using at least one of the following: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of the parts, a male portion of one part mounted into a female portion of the other part, a key introduced into a lock being portions of the parts, band, and other mechanical connecting members.

According to yet another embodiment the medical device could be adapted to be fixated to the caput femur using at least one of the following: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of the parts, a male portion of one part mounted into a female portion of the other part, a key introduced into a lock being portions of the parts, band, and other mechanical connecting members.

According to yet another embodiment the artificial caput femur surface could be adapted to be fixated to the caput femur without penetration of the cortex of caput femur or the femur bone.

According to yet another embodiment the medical device could be adapted to be fixated by means of an elastic member exerting a squeezing force on the caput femur.

According to yet another embodiment the elastic member exerting a squeezing force on the caput femur could be the locking member. In any of the embodiments herein, the locking member could be an element selected from: a cord, a wire and a band.

A medical device for implantation in a hip joint of a patient is further provided. The hip joint has a caput femur hip joint surface partly being the contacting surface of the hip joint, the hip joint further having a collum femur, having a first axial distribution leading to a caput femur, wherein a center axis of the first axial distribution of the collum femur and the caput femur, being the caput and collum femur center axis. The collum femur is placed more distal than caput femur. The medical device further comprises an artificial caput femur surface being hollow and having a major opening adapted to be directed distally and being adapted to replace a caput femur hip joint surface. The artificial caput femur surface further having a medical device caput center axis passing through the major opening, being aligned with the caput and collum femur center axis, when the medical device is implanted in a functional position in the hip joint. The medical device further comprises a central part and a surrounding part, the central part being aligned with the medical device center axis and the surrounding part surrounding the surface of the caput femur not including the central part. The medical device further comprises: an inner surface adapted to have a first distal distance extending perpendicularly from the medical device caput center axis to the inner surface of the surrounding part of the artificial caput femur surface. The distal distance is shorter than a second proximal distance extending perpendicularly from the medical device caput center axis to the inner surface of the artificial caput femur surface. The second proximal distance extends from a more proximal position on the medical device caput center axis than the first distal distance, being the second proximal distance, when said artificial caput femur surface is implanted in said functional position in the hip joint. The medical device further comprising a locking member for implantation in a hip joint of a patient. The locking member is adapted to assist in the fixation of the medical device to the collum and/or caput femur. The locking member comprises an element adapted to lock the artificial caput femur surface such that the caput femur remains clasped and restrained in said artificial caput femur surface.

According to one embodiment the medical device is adapted to lock in at least a first and a second locking position. The locking member is adapted to; in said first locking position, lock a first artificial caput femur surface having at least one extending portion, to a first size caput femur and/or collum femur, and in said second locking position, lock a second artificial caput femur surface having at least one extending portion, to a second smaller size caput and/or collum femur.

According to another embodiment, the locking member is adapted to lock in at least a first and a second locking position, wherein said locking member is adapted to, in said first locking position, lock an artificial caput femur surface having at least one extending portion to a caput and/or collum femur, and wherein said locking member is adapted to, in said second locking position, lock said artificial caput femur surface tighter to the caput and/or collum femur.

In yet another embodiment, the locking member is adapted to lock in at least a first and a second locking position, wherein the locking member is adapted to; in the first locking position, lock an artificial caput femur surface having at least one extending portion, to a first size caput and/or collum femur, and in said second locking position, lock said artificial caput femur surface, to a second smaller size caput femur and/or collum femur.

The hip joint has a caput femur integrated with a collum femur having a center axis extending longitudinal along the collum and caput femur in the center thereof. The collum femur is placed more distal than caput femur. The medical device system comprises two or more medical devices, wherein each of the medical devices comprises an artificial caput femur surfaces being hollow, having a major opening adapted to be directed distally, when said medical device is implanted. The artificial caput femur surface is adapted to replace a caput femur hip joint surface, further having; a medical device caput center axis passing through said major opening, being aligned with the caput femur center axis, when said medical device is implanted in a functional position in the hip joint. The medical device comprises a central part and a surrounding part, the central part being aligned with the medical device center axis and the surrounding part surrounding the surface of the caput femur not including the central part. The medical device further comprises; an inner surface adapted to have a first distal distance extending perpendicularly from said medical device caput center axis to said inner surface of the surrounding part of said artificial caput femur surface. The first distal distance is shorter than a second proximal distance extending perpendicularly from the medical device caput center axis to said inner surface of said artificial caput femur surface, said second proximal distance extending from a more proximal position on said medical device caput center axis than said first distal distance, being the second proximal distance, when said artificial caput femur surface is implanted in said functional position in the hip joint. The medical device further comprising a locking member for implantation in a hip joint of a patient. The locking member is adapted to assist in the fixation of said medical device to the collum and/or caput femur, wherein said locking member comprises an element adapted to lock said artificial caput femur surface such that the caput femur remains clasped and restrained in said artificial caput femur surface, and at least one of said artificial caput femur surfaces has a size adapted to replace the caput femur hip joint surface of a corresponding size.

According to yet another embodiment, the medical device system further comprises two or more locking members. The two locking members have different sizes when in their locking position, and thus being adapted to lock different artificial caput femur surfaces of different sizes to a caput femur, or an artificial caput femur surfaces to caput femur of different sizes, such that the caput femur remains clasped and restrained in the artificial caput femur surface, when locked by one of the two or more locking members having the matching size.

According to another embodiment, the locking member is adapted to lock in at least a first and a second locking position. The locking member is adapted to; in said first locking position, lock a first artificial caput femur surface having at least one extending portion to a first size caput femur and/or collum femur, and in said second locking position, lock a second artificial caput femur surface having at least one extending portion, to a second smaller size caput and/or collum femur.

According to yet another embodiment the locking member is adapted to lock in at least a first and a second locking position. The locking member is adapted to, in said first locking position, lock an artificial caput femur surface having at least one extending portion to a caput and/or collum femur, and wherein said locking member is adapted to, in said second locking position, lock said artificial caput femur surface tighter to the caput and/or collum femur.

According to another embodiment, the locking member is adapted to lock in at least a first and a second locking position, wherein said locking member is adapted to; in said first locking position, lock an artificial caput femur surface having at least one extending portion, to a first size caput and/or collum femur, and in said second locking position, lock said artificial caput femur surface, to a second smaller size caput femur and/or collum femur.

In one embodiment the locking member comprises a loop-shaped element adapted to be connected in situ for creating said loop shape surrounding the caput and/or collum femur, when implanted.

According to yet another embodiment, a loop shaped element is adapted to have a first locking state, in which said loop shape has a first inner circumference, and wherein said loop shaped element is further adapted to have a second locking state, in which said loop shaped element has a second smaller inner circumference.

The medical device system could according to another embodiment have a loop shaped element adapted to further have a third locking state, in which said loop shape has a third inner circumference being smaller than said first and second inner circumference.

In yet another embodiment, the locking member is further adapted to be arranged in an area extending a distance beyond the maximum diameter of the caput femur.

The loop shaped element could in any of the embodiments herein be an element selected from: a cord, a wire and a band.

In yet another embodiment, the locking member could comprise a first and second engagement member. The first engagement member could be adapted to engage the second engagement member, when implanted.

In yet another embodiment, the first and second engagement members are adapted to mechanically self connect by introducing a male part of said first engagement member into a female part of said second engagement member.

In yet another embodiment of the medical device system, the first and second engagement members are fixated to the artificial caput femur surface on the inside thereof.

The first and second engagement members could according to another embodiment be fixated to the artificial caput femur surface on the outside thereof.

According to yet another embodiment, the artificial caput femur surface could comprise at least one slit, and the first and second engagement members could be fixated to the artificial hollow caput femur surface on two different sides of a slit, respectively.

According to other embodiments the first and second engagement members could be fixated to the artificial hollow caput femur surface, on extending portion thereof.

The loop shaped element could comprise a first and second end, and the first and second end could be adapted to be connected to form the loop shaped element using an engagement member comprising two pivotable locking parts.

According to another embodiment, the first locking part is pivotably attached both to the first end of the locking member and to the second locking part.

In yet other embodiments the second locking part could be attached to the first locking part in a point arranged substantially in the middle of said first locking part.

In yet other embodiments, the first and second locking member ends are could be arranged overlapping each other when locked together.

According to yet another embodiment, the locking member could be adapted to be fixated to the artificial caput femur surface, perpendicularly to the center axis of the caput and collum femur and adapted to partially surround the caput and/or collum femur and clasp the caput and/or collum femur.

In yet other embodiments the locking member could be made from an elastic material, for enabling the locking member to be placed onto the artificial caput femur surface, clasping the caput and/or collum femur.

The locking member could comprise a first and second portion, the first and second portions could be pivotably connected at a hinge. Wherein the first and second portions could be adapted to pivot for enabling the locking member to be placed partially surrounding the artificial caput femur.

In yet other embodiments the locking member could further comprise a locking element adapted to lock the connection between the first and second portion, such that the locking member can be locked clasping the caput and/or collum femur, when implanted.

In some embodiments disclosed herein the locking member comprises at least one mechanical fixating member adapted to be placed in contact with the artificial caput femur surface, and in the bone of the collum and/or caput femur, thereby fixating the artificial caput femur surface to the collum and/or caput femur.

According to yet another embodiment, the at least one mechanical fixating member is adapted to travel from one point on the artificial caput femur surface, through a portion of the bone of the collum and/or caput femur, and to a second point on the artificial caput femur surface.

According to yet another embodiment, the length of the mechanical fixating member is changeable, and wherein said mechanical fixating member thus can be shortened for squeezing and further fixating the artificial caput femur surface to the collum and/or caput femur.

The mechanical fixating member could according to one embodiment comprise a threaded portion.

The mechanical fixating member could according to another embodiment be adapted to be placed in contact with the artificial caput femur surface at the extending portion thereof.

A medical device system for implantation in a hip joint of a patient is further provided. The hip joint has a caput femur integrated with a collum femur having a center axis extending longitudinal along the collum and caput femur in the center thereof. The medical device system could comprise an artificial hollow caput femur surface comprising at least one extending portion adapted to clasp a portion of the caput and/or collum femur, and a locking member adapted to assist in the fixation of the medical device to a portion of the caput and/or collum femur. The locking member could comprise an element adapted to lock the artificial caput femur surface such that the caput femur remains clasped and restrained in said artificial caput femur surface.

In yet another embodiment, the hollow artificial caput femur surface is adapted to at least partly cover the caput femur, when implanted in a functional position in the hip joint.

In yet another embodiment, the artificial caput femur surface could be adapted to be placed in an acetabulum bowl, or an artificial replacement therefore, when implanted in the functional position in the hip joint.

The artificial caput femur surface could in other embodiments be adapted to have a changeable first distal distance, thus being adapted to be mounted onto the caput femur, when implanted in the hip joint.

In other embodiments, the artificial caput femur surface could be adapted to have the maximum second proximal distance, extending perpendicularly from said medical device caput center axis to said inner surface of said artificial caput femur surface, wherein said maximum second proximal distance is located on a part of said medical device caput center axis located more proximal than said major opening, when said artificial caput femur surface is mounted in said functional position in the hip joint. The artificial caput femur surface could further be adapted to have the closest first distal distance extending perpendicularly from said medical device caput center axis to said inner surface of said artificial caput femur surface, being smaller than the maximum second proximal distance. The maximum second proximal distance could be extending from the medical device caput center axis, more proximal than the closest first distal distance, when implanted in said functional position in the hip joint.

According to yet another embodiment, the medical device could further comprise at least one slit in said artificial caput femur surface allowing said device to vary the diameter of a major opening, thus allowing the device to be mounted on said caput femur. The artificial caput femur surface could comprise a major opening having at least partly, a diameter or cross sectional distance adapted to be changed in at least one of the following ways: increase to be able to mount said medical device on the caput femur, decrease to mechanically fixate and enable a stable position of said medical device on the caput femur when mounted thereon.

The closest distance from the inner surface of said first extending portion to said caput and collum femur center axis, perpendicular to said caput and collum femur center axis could be adapted to be adjustable by said extending portion comprising at least one of the elements selected from a list consisting of: an elastic portion, a bendable portion, a flexible portion, a compressible portion, and a movable portion.

According to yet another embodiment, the closest distance from the inner surface of the first extending portion to the caput and collum femur center axis, perpendicular to said caput and collum center axis, is adapted to be adjusted by said locking member.

In yet another embodiment, the medical device could comprise at least two parts adapted to be connected to each other during a surgical or arthroscopic/laparoscopic procedure.

The artificial caput femur surface could in some embodiments be incomplete in its surface distribution.

The artificial caput femur surface could in other embodiments be adapted to be fixated to the caput femur without penetration of the cortex of caput femur or the femur bone.

In yet other embodiments, the medical device could be adapted to be fixated by means of an elastic member exerting a squeezing force on the caput femur.

In yet other embodiments of the medical device, the elastic member could be adapted to exert a squeezing force on the caput femur is the said locking member.

According to other embodiments, the locking member could be adapted to lock in at least a first and a second locking position, and the locking member could be adapted to; in the first locking position, lock a first artificial caput femur surface having at least one extending portion, to a first size caput femur and/or collum femur, and in the second locking position, lock a second artificial caput femur surface having at least one extending portion, to a second smaller size caput and/or collum femur.

In yet other embodiments the locking member could be adapted to lock in at least a first and a second locking position, and the locking member could be adapted to, in said first locking position, lock an artificial caput femur surface having at least one extending portion to a caput and/or collum femur. The locking member could further be adapted to, in said second locking position, lock said artificial caput femur surface tighter to the caput and/or collum femur.

In yet other embodiments the locking member could be adapted to lock in at least a first and a second locking position, wherein said locking member is adapted to; in said first locking position, lock an artificial caput femur surface having at least one extending portion, to a first size caput and/or collum femur, and in said second locking position, lock said artificial caput femur surface, to a second smaller size caput femur and/or collum femur.

In yet other embodiments the locking member comprises a loop-shaped element adapted to be connected in situ for creating said loop shape surrounding the caput and/or collum femur, when implanted.

The loop shaped element could be adapted to have a first locking state, in which said loop shape has a first inner circumference, wherein said loop shaped element is further adapted to have a second locking state, in which said loop shaped element has a second smaller inner circumference.

The loop shaped element could be adapted to further have a third locking state, in which said loop shape has a third inner circumference being smaller than said first and second inner circumference. The locking member could further be adapted to be arranged in an area extending a distance beyond the maximum diameter of the caput femur.

In other embodiments, the loop shaped element could be an element selected from: a cord, a wire and a band.

The locking member according to any one of the embodiments could comprise a first and second engagement member, and wherein said first engagement member is adapted to engage said second engagement member, when implanted. The first and second engagement members could be adapted to mechanically self connect by introducing a male part of said first engagement member into a female part of said second engagement member.

According to another embodiment, the first and second engagement members could be fixated to the artificial caput femur surface on the inside thereof.

In yet other embodiments, the first and second engagement members are fixated to the artificial caput femur surface on the outside thereof.

In yet other embodiments the artificial caput femur surface could comprise at least one slit, wherein said first and second engagement member could be fixated to the artificial hollow caput femur surface on two different sides of the slit, respectively.

The first and second engagement members could be fixated to the artificial hollow caput femur surface, on extending portion thereof.

According to other embodiments, the loop shaped element could comprise a first and second end, wherein said first and second ends could be adapted to be connected to form the loop shaped element using an engagement member comprising two pivotable locking parts.

In yet other embodiments, the first locking part is pivotably attached both to the first end of the locking member and to said the second locking part.

In other embodiments, the locking part could be attached to the first locking part in a point arranged substantially in the middle of said first locking part.

The first and second locking member ends could be arranged overlapping each other when locked together.

In other embodiments a locking member could be adapted to be fixated to the artificial caput femur surface, perpendicularly to said center axis of the caput and collum femur and adapted to partially surround the caput and/or collum femur and clasp the caput and/or collum femur.

In some embodiments, the locking member is made from an elastic material, for enabling the locking member to be placed onto the artificial caput femur surface, clasping the caput and/or collum femur.

The locking member could comprise a first and second portion, and the first and second portion could be pivotably connected at a hinge, and wherein said first and second portions are adapted to pivot for enabling the locking member to be placed partially surrounding the artificial caput femur.

In yet other embodiments the locking member could further comprise a locking element adapted to lock the connection between said first and second portion, such that said locking member can be locked clasping the caput and/or collum femur, when implanted.

The locking member could comprise at least one mechanical fixating member adapted to be placed in contact with the artificial caput femur surface, and in the bone of the collum and/or caput femur, thereby fixating the artificial caput femur surface to the collum and/or caput femur.

In yet other embodiments, the at least one mechanical fixating member could be adapted to travel from one point on the artificial caput femur surface, through a portion of the bone of the collum and/or caput femur, and to a second point on the artificial caput femur surface.

The length of the mechanical fixating member could be adapted to be changeable, such that the mechanical fixating member can be shortened for squeezing and further fixating the artificial caput femur surface to the collum and/or caput femur.

A locking member system comprising two or more locking members according to any one of the embodiments herein is further provided. The two locking members have different sizes, when in their locking position. The locking members could be adapted to lock an artificial caput femur surface of a corresponding size, selected from different sizes thereof.

The locking member could comprise an artificial caput femur surface surface, comprising an extending portion, wherein said at least one extending portion is constructed according to at least one of the following alternatives; a) circumferentially extends discontinuously along said equator line and b) extends with different distal extension in different extending portions or part of such portion of said circumferential extension.

The locking member could comprise a lock holding member to hold said locking member in position onto said extending portion of the artificial caput femur surface surface.

The locking member could be integrated in the bearing surface of the artificial caput femur surface to hold said locking member in position onto said extending portion of the artificial caput femur surface.

The hip joint has a collum femur, having a first axial distribution leading to a caput femur, wherein said collum femur is placed distal to the caput femur, a center axis of the collum and caput femur in line with the first axial distribution being the caput femur center axis, wherein the caput femur has a substantially ball shaped configuration with an outer maximum radius perpendicular to the caput femur center axis, the caput femur being placed in a bowl shaped acetabulum, having an opening, wherein the bowl shaped acetabulum has a second axial distribution with an acetabulum center axis from the center of the bottom of the acetabulum bowl and following the center of the bowl towards the center of the opening of the bowl, towards the caput femur, wherein the acetabulum bowl has an inner maximum radius perpendicular to the acetabulum center axis, wherein the caput femur center axis is in line/aligned with the acetabulum center axis, in a special centered position, when the caput femur is placed; aligned, centered and symmetrical in the acetabulum bowl in the hip joint, the aligned center axis is defined as the hip joint center axis, wherein the caput femur and the acetabulum has one hip joint surface each, placed towards and contacting each other, wherein the hip joint surfaces carrying weight in the hip joint are the weight carrying surfaces, wherein the outer maximum radius of the caput femur is forming a circular extending, maximum caput femur radius circle, extending perpendicular to the hip joint center axis, defining a maximum caput femur radius cross-section perpendicular to the hip joint center axis, wherein: said medical device comprises at least one artificial hip joint surface, adapted to at least partly replace at least one of the hip joint surfaces, said artificial hip joint surface at least partly being hollow and having an inner and outer surface, wherein said artificial hip joint surface has an artificial hip joint surface center axis aligned with the hip joint center axis when the hip joint is placed in the special centered position, when at least one of said artificial hip joint surfaces is implanted in the hip joint, with the caput femur or an artificial caput femur surface placed; aligned, centered and symmetrical in the acetabulum bowl or an artificial acetabulum surface in the hip joint, wherein said medical device comprises a central part and a surrounding part, the central part being aligned with the artificial hip joint surface center axis and the surrounding part surrounding the surface of the caput femur or an artificial caput femur surface not including the central part, wherein the caput femur or an artificial caput femur surface, has a maximum caput femur radius cross-section, in which the outer maximum radius of the caput femur or said artificial caput femur surface is forming a circular extending maximum caput femur or artificial caput femur radius circle, extending perpendicular to the hip joint center axis, defining the maximum caput femur radius cross-section perpendicular to the hip joint center axis or perpendicular to said artificial hip joint surface center axis, when the hip joint is placed in said special centered position, wherein the surrounding part of said at least one artificial hip joint surface comprises at least one first extending portion of the artificial hip joint surface for extending in distal direction at least partly beyond the maximum caput femur radius cross-section, when the hip joint is placed in said special centered position, when at least one of the artificial hip joint surfaces is implanted in the hip joint, wherein said at least one first beyond part is adapted to have a closest perpendicular distance to said artificial hip joint surface center axis, being smaller than an inner maximum distance, extending perpendicularly from said artificial hip joint surface center axis to said inner surface of said artificial hip joint surface, when the hip joint is placed in the above mentioned special centered position and said artificial hip joint surface is placed in a functional position in the hip joint, thus adapted to create and creating a more stable position of said artificial hip joint surface when mounted in the hip joint.

The hip joint has a
caput femur hip joint surface partly being the contacting surface of the hip joint, the
hip joint further having a collum femur, having a first axial distribution leading to a
caput femur, wherein a center axis of the first axial distribution of the the collum
femur and the caput femur, being the caput femur center axis, wherein the collum
femur is placed more distal than caput femur, wherein; said medical device comprises an artificial caput femur surface being hollow,
having a major opening adapted to be directed towards the caput femur or a
surgically modified caput femur, wherein said artificial caput femur surface is
adapted to replace a caput femur hip joint surface, wherein said artificial caput femur surface further having;

a medical device caput center axis passing through said
major opening,
being aligned with the caput femur center axis, when said
medical device is
implanted in a functional position in the hip joint, wherein
said medical
device comprises a central part and a surrounding part, the
central part
being aligned with the medical device center axis and the
surrounding part
surrounding the surface of the caput femur or the surgically modified caput
femur not including the central part, and wherein said
medical device
further comprising
an inner surface adapted to have a first distal distance
extending
perpendicularly from said medical device caput center
axis to said inner
surface of the surrounding part of said artificial caput
femur surface, said
first distal distance being shorter than a second proximal
distance
extending perpendicularly from said medical device caput
center axis to
said inner surface of said artificial caput femur surface,
said second
proximal distance extending from a more proximal position on said
medical device caput center axis than said first distal
distance, being the
second proximal distance, when said artificial caput femur
surface is
implanted in said functional position in the hip joint.

6. The medical device for implantation in a hip joint of a patient according to any of the preceding claims, the hip joint having
an acetabulum, being a bowl shaped contacting surface of
the hip joint comprising
a substantially circular major opening in distal direction
of the acetabulum in the
hip joint and a bottom center point in said bowl shaped
acetabulum proximally in
the hip joint, wherein an acetabulum center axis extends
from the bottom point
through the center point of the substantially circular
opening, wherein the
acetabulum has a weight carrying surface contacting a
ball shaped caput femur
located in the acetabulum bowl in the hip joint, wherein
the caput femur is
connected to the collum femur, and the collum femur has
a center axis aligned
with a caput femur center axis, wherein;
said medical device comprises an artificial acetabulum
surface adapted to
replace the weight carrying surface of the acetabulum,
wherein said artificial
acetabulum surface is hollow and has a major acetabulum
opening adapted to
be directed towards the caput femur or an artificial
replacement of at least the surface of the caput femur,
wherein said artificial acetabulum surface is adapted to
receive a caput femur or an artificial replacement of at
least the surface of the caput femur, in said hollow
artificial acetabulum surface, when implanted in the hip
joint, said artificial acetabulum surface having; a medical device acetabulum center axis, adapted to be
aligned with the acetabulum center axis, when said
artificial acetabulum surface is placed in the hip joint,
and an inner surface adapted to have a first distal
distance extending perpendicularly from said medical
device acetabulum center axis, to said inner surface of
said artificial acetabulum surface, said first distal distance being shorter than a second proximal distance
extending perpendicularly from said medical device
acetabulum center axis to said inner surface of said
artificial acetabulum surface, said second proximal
distance extending from a more proximal position on
said medical device acetabulum center axis than said
first distal distance, when said artificial acetabulum
surface is implanted functionally in the hip joint,
wherein said artificial acetabulum surface is adapted to
receive in the hollow artificial acetabulum surface the
caput femur or an artificial replacement of at least the
surface of the caput femur, when implanted in the hip
joint, for achieving a functional hip joint.

Method

A method for implantation of a locking member in a hip joint of a patient is further provided, the hip joint having a caput femur integrated with a collum femur having a center axis extending longitudinal along the collum and caput femur in the center thereof, the method comprise the following steps;
performing an operation in a hip joint surgically or
arthroscopically,
placing an artificial hollow caput femur surface mounted
onto caput femur,
placing a locking member for assisting in the fixation of
the artificial caput femur surface, wherein said artificial
caput femur surface comprises at least one extending
portion adapted to clasp a portion of the caput and/or
collum femur,
clasping with the least one extending portion a portion of
the caput and/or collum femur,
and wherein said locking member comprises an element
adapted to lock said artificial caput femur surface such
that the caput femur remains clasped and restrained in
said artificial caput femur surface,
locking by said locking member element said artificial
caput femur surface such that the caput femur is
remaining clasped and restrained in said artificial caput
femur surface.

The method comprising the steps of; —locking in said first locking position, and—locking in second position locking tighter the artificial caput femur surface with at least one extending portion, to the caput and/or collum femur.

According to another embodiment, the locking member is adapted to lock in at least a first and a second locking position, the method comprising the steps of; —locking in said first locking position a first artificial hollow caput femur surface, and—locking in second position a second smaller artificial caput femur surface with at least one extending portion, to the caput and/or collum femur.

The method using a locking member according to any one of the preceding embodiments, wherein said locking member comprises a loop-shaped element, the method comprise the step of; locking in situ said loop shape surrounding the caput and/or collum femur.

The method according to any of the embodiments, locking said loop shaped element in a first locking state, in which said loop shape has a first inner circumference, and locking said loop shaped element in a second locking state, in which said loop shaped element has a second smaller inner circumference.

The method using the locking member according to any of the embodiments, wherein said locking member further comprises a medical device comprising, an artificial caput femur surface being hollow, having a major opening adapted to be directed distally and being adapted to replace a caput femur hip joint surface, wherein said artificial caput femur surface further having;
- a medical device caput center axis passing through said major opening, being aligned with the caput and collum femur center axis, when said medical device is implanted in a functional position in the hip joint, wherein said medical device comprises a central part and a surrounding part, the central part being aligned with the medical device center axis and the surrounding part surrounding the surface of the caput femur not including the central part, and wherein said medical device further comprises; an inner surface adapted to have a first distal distance extending perpendicularly from said medical device caput center axis to said inner surface of said surrounding part of said artificial caput femur surface, said first distal distance being shorter than a second proximal distance extending perpendicularly from said medical device caput center axis to said inner surface of said artificial caput femur surface, said second proximal distance extending from a more proximal position on said medical device caput center axis than said first distal distance, being the second proximal distance, when said artificial caput femur surface is implanted in said functional position in the hip joint, the artificial caput femur surface comprise a lock holding member for holding the locking member in its position, the method involves the step of;
- placing the artifical caput femur surface onto caput femur during a surgical or arthroscopical operation, —placing the locking member and—locking said artifical caput femur surface to caput femur, —holding said locking member in place by said lock holding member.

A method for implantation at least one medical device in a hip joint of a patient, the hip joint having a caput femur integrated with a collum femur having a center axis extending longitudinal along the collum and caput femur in the center thereof, wherein the collum femur is placed more distal than caput femur, wherein;
- said medical device system comprises two or more medical devices, wherein each of the medical devices comprising:
- an artificial caput femur surfaces being hollow, having a major opening adapted to be directed distally, when said medical device is implanted, wherein said artificial caput femur surface is adapted to replace a caput femur hip joint surface, further having;
- a medical device caput center axis passing through said major opening, being aligned with the caput femur center axis, when said medical device is implanted in a functional position in the hip joint, wherein said medical device comprises a central part and a surrounding part, the central part being aligned with the medical device center axis and the surrounding part surrounding the surface of the caput femur not including the central part, and wherein said medical device further comprises;
- an inner surface adapted to have a first distal distance extending perpendicularly from said medical device caput center axis to said inner surface of the surrounding part of said artificial caput femur surface, said first distal distance being shorter than a second proximal distance extending perpendicularly from said medical device caput center axis to said inner surface of said artificial caput femur surface, said second proximal distance extending from a more proximal position on said medical device caput center axis than said first distal distance, being the second proximal distance, when said artificial caput femur surface is implanted in said functional position in the hip joint, and a locking member for implantation in a hip joint of a patient, wherein said locking member is adapted to assist in the fixation of said medical device to the collum and/or caput femur, wherein said locking member comprises an element adapted to lock said artificial caput femur surface such that the caput femur remains clasped and restrained in said artificial caput femur surface, wherein at least one of said artificial caput femur surfaces has a size adapted to replace the caput femur hip joint surface of a corresponding size, wherein the method includes the step of; surgically or arthroscopically implanting two or more artificial caput femur surfaces to find the right size to lock onto the caput femur.

The method according to any of the embodiments further comprising two or more locking members, wherein the two locking members have different sizes, when in their locking position, and thus being adapted to lock different artificial caput femur surfaces of different sizes to a caput femur, or an artificial caput femur surfaces to caput femurs of different sizes, such that the caput femur remains clasped and restrained in the artificial caput femur surface, when locked by one of the two or more locking members having the matching size, the method involves the step of; using two or more locking members to lock the artificial caput femur surface of the correct size to the caput femur.

According to one embodiment, the at least one extending portion is mounted according to at least one of the following alternatives:
- a) extending circumferentially discontinuously along said equator line having enough circumferential distance lacking any extending portion and b) extending with different distal extension in different extending portions or part of such portion of said circumferential extension.

Please note that any embodiment or part of embodiment, feature, method, associated system, part of system described herein or in the associated figures may be combined in any way.

BRIEF DESCRIPTION OF DRAWINGS

The invention is now described, by way of example, with reference to the accompanying drawings, in which:

FIG. 7 shows an artificial caput femur surface in section having a major opening adapted to travel over and beyond the maximum diameter of the caput femur,
FIG. 8a shows an artificial caput femur surface 45 according to a first embodiment,
FIG. 8b shows the artificial caput femur surface when fixated to the caput femur,
FIG. 9 shows an artificial acetabulum surface according to a first embodiment,
FIG. 13a shows a medical device with an integrated locking member according to one embodiment,
FIG. 13b shows a medical device with an integrated locking member according to another embodiment,
FIG. 14 shows an embodiment of a medical device and a mechanical fixating member.

DETAILED DESCRIPTION

Figure 1:
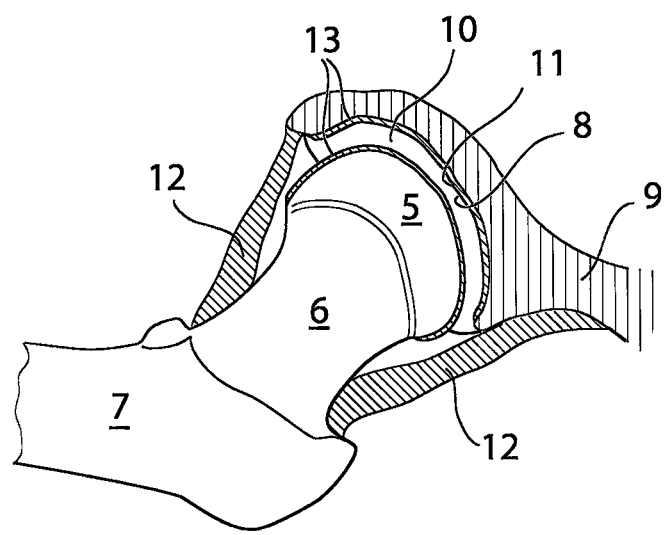
FIG. 1 shows the hip joint of a human patient in section.

The hip joint is a synovial ball and socket joint which permits a large motion range for allowing a plurality of different movements of the lower limb. From a neutral position the following movements of the hip joint are normally possible: Lateral or external rotation, 30° with the hip extended, 50° with the hip flexed, medial or internal rotation 40°, extension or retroversion 20°, flexion or anteversion 140°, abduction 50° with hip extended, 80° with hip flexed, adduction 30° with hip extended, 20° with hip flexed.

When replacing the natural hip joint with an artificial, the depth of the artificial acetabulum will affect the motion range of the hip joint, the deeper the acetabulum bowl is made the more restrictive it is to the motion range. A deeper bowl has the advantage of reducing the risk of hip joint luxation, the risk of which is a major drawback with prosthetic hips of today.

The caput and collum femur are to be understood as the proximal portion of the femoral bone. In orthopedic surgery the caput and/or collum femur is sometimes surgically modified, e.g. bone is removed to adapt the proximal portion of the femoral bone to a particular prosthesis. For the purpose of this application the caput/collum femur are to be understood as either the natural caput/collum femur or a surgically modified caput/collum femur.

The anatomy of the hip joint and its surroundings is further disclosed in: Marieb et al., Human Anatomy, 2003, Benjamin Cummings, San Francisco, pages 195-202 and in Moore et al., Clinically oriented anatomy, 1999, Lippincott, Williams & Wilkins, Baltimore, pages 501-653, both hereby incorporated by reference.

Centrally in the body should herein be understood as a point of reference located at the intersection of the Median plane and the Coronal plane and in the center part of the heart along a longitudinal axis (Caudal—Cranial). Proximal and distal are direction or location terms used in relation to said point centrally in the body and hence a distal point is a point farther away from the central point in relation a proximal point of the same structure. Other anatomical terms used herein are further described in Moore et al., Clinically oriented anatomy, 1999, Lippincott, Williams & Wilkins, Baltimore, pages 2-10, which is hereby incorporated by reference.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

Everyday activities is to be understood as activities which are not connected to any extreme movements, such that some physical sports require. For example, everyday activities comprise: walking, sitting, cycling etc.

The functional position of an implantable medical device or prosthesis is the position in which the hip joint can perform functional hip movements. The final position is to be understood as a functional position in which the medical device needs no further position change.

Elasticity is to be understood as a materials ability to deform in an elastic way.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Stiffness is to be understood as the resistance of an elastic body to deformation by an applied force.

Biocompatible material is to be understood as being a material with low level of immune response. Biocompatible materials are sometimes also referred to as biomaterials. Analogous is biocompatible metals a biocompatible metal with low immune response such as titanium or tantalum. The biocompatible metal could also be a biocompatible alloy comprising at least one biocompatible metal.

Form fitting is to be understood as an element having a part or section which is adapted to enable a mechanical connection of said element to at least one other element using said part or section. Form fitted structure is a structure of an element which enables form fitting.

In the following a detailed description of embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

FIG. 1 shows the hip joint of a human patient in section. The hip joint comprises a caput femur 5 placed at the very top of collum femur 6 which is the top part of the femoral bone 7. The caput femur is in connection with the acetabulum 8 which is a bowl shaped part of the pelvic bone 9. Both the caput femur surface 10 and the acetabulum surface 11 are covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 2:
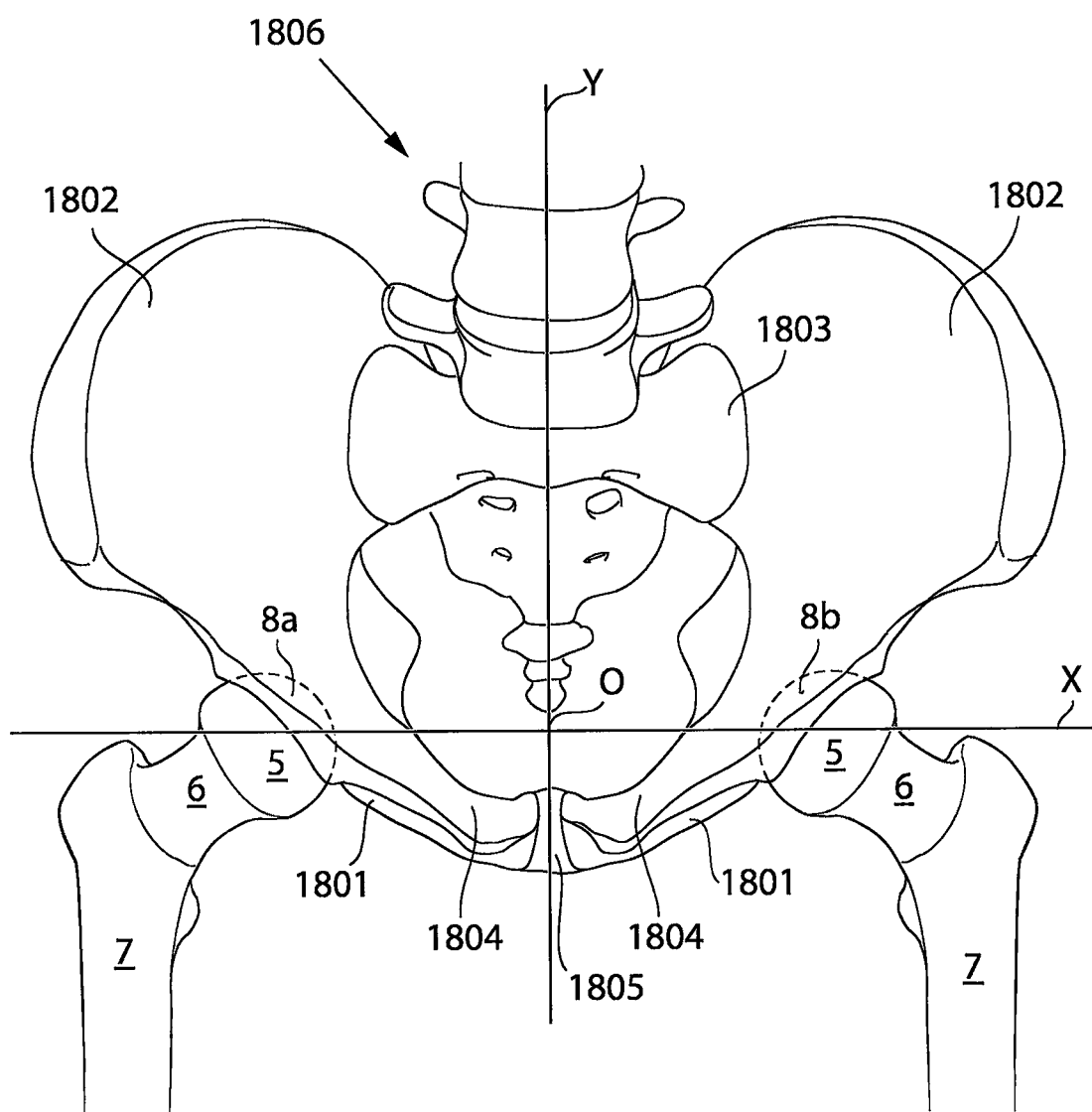
FIG. 2 shows the pelvis in a frontal view.

FIG. 2 shows the pelvis in a frontal view. Pelvis comprises the right and left hip bone making up the pelvic bone, in turn comprising the Sacrum 1803, Ilium 1802, Pubis 1804 and Ischium 1801. The hip joint houses the right and left acetabulum 8a,b placed laterally and distally in the pelvis. The acetabulum 8a,b being a spherically shaped cavity in the hip bones making up one of the parts of the hip joint, the acetabulum 8a,b being adapted to house the caput femur 5, being the proximal portion of the femoral bone 7 having a spherical contacting surface adapted to be placed in the acetabulum 8a,b and thus creating the operable hip joint. The pelvis has a lateral-medial axis X extending substantially from the bottom of the left acetabulum 8a to the bottom of the right acetabulum 8b, the pelvis further having a proximal-distal Y axis extending perpendicular to said lateral-medial axis, centrally and substantially along the length of the patient, passing the dorsal portions of the pubic symphysis 1805 and substantially following the spinal cord 1806, intersecting the lateral-medial axis X.

Figure 3:
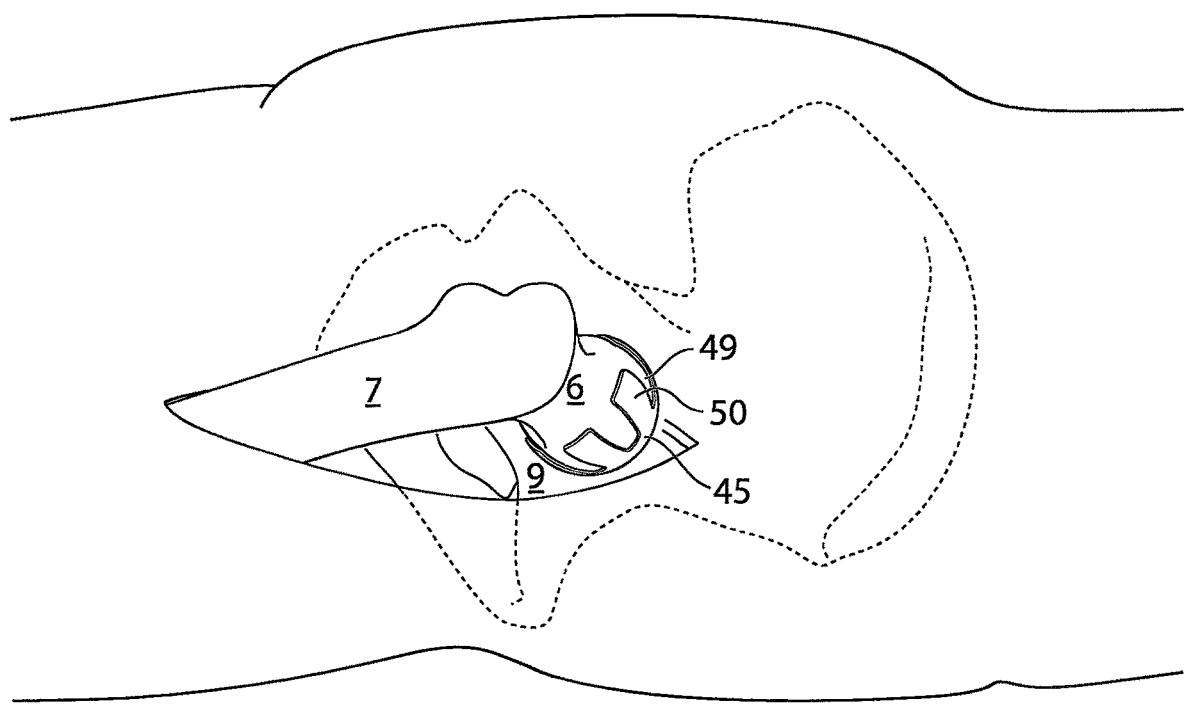
FIG. 3 shows the placing of an artificial caput femur surface on the caput femur in conventional surgery.

FIG. 3 shows the placing of an artificial caput femur surface 45 on the caput femur in conventional surgery. The artificial caput femur according to this embodiment comprises slits 49 and arms 50 making the structure of the artificial caput femur surface flexible for clasping the caput femur 5 and going beyond the maximum diameter of the caput femur 5. Furthermore the artificial caput femur surface 45 can be inserted into a hip joint through a hole smaller than the full functional size of the artificial caput femur surface 45, enabling a less invasive surgical procedure.

Figure 4:
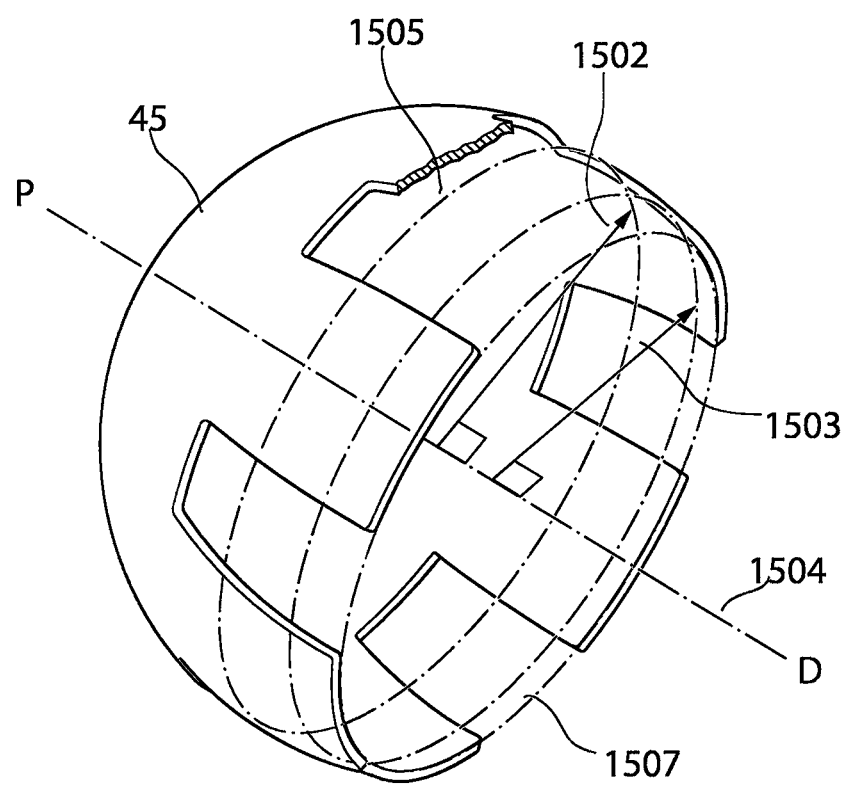
FIG. 4 shows a medical device for implantation in a hip joint of a patient.

FIG. 4 shows a medical device for implantation in a hip joint of a patient. The medical device comprises an artificial caput femur surface 45 being hollow, having a major opening 1507 adapted to be directed towards the caput femur or a surgically modified caput femur when implanted in the hip joint. A medical device caput center axis 1504 passes through the major opening 1507, when said medical device is implanted in a functional position in the hip joint. The medical device comprises an inner surface adapted to have a first distal distance 1503 extending perpendicularly from said medical device caput center axis 1504 to said inner surface of said artificial caput femur surface 45. The first distal distance 1503 being shorter than a second proximal distance 1502 extending perpendicularly from said medical device caput center axis 1504 to said inner surface of said artificial caput femur surface 45. The second proximal distance 1502 extending from a more proximal position on the medical device caput center axis 1504 than the first distal distance 1503, when the artificial caput femur surface 45 is implanted in a functional position in the hip joint. The maximum first distal distance 1503 is located on a part of said medical device caput center axis 1504 substantially located more proximal than said major opening 1507, when said artificial caput femur surface 45 is mounted in the functional position in the hip joint. The artificial caput femur surface 45 is adapted to have a closest second proximal 1502 distance extending perpendicularly from said medical device caput center axis 1504 to said inner surface of said artificial caput femur surface 45, being smaller than the maximum first distal distance 1503. The maximum first distal distance 1503 is extending from the medical device caput center axis 1504 more distal than the closest second proximal distance 1502, when implanted in a functional position in the hip joint.

Figure 5:
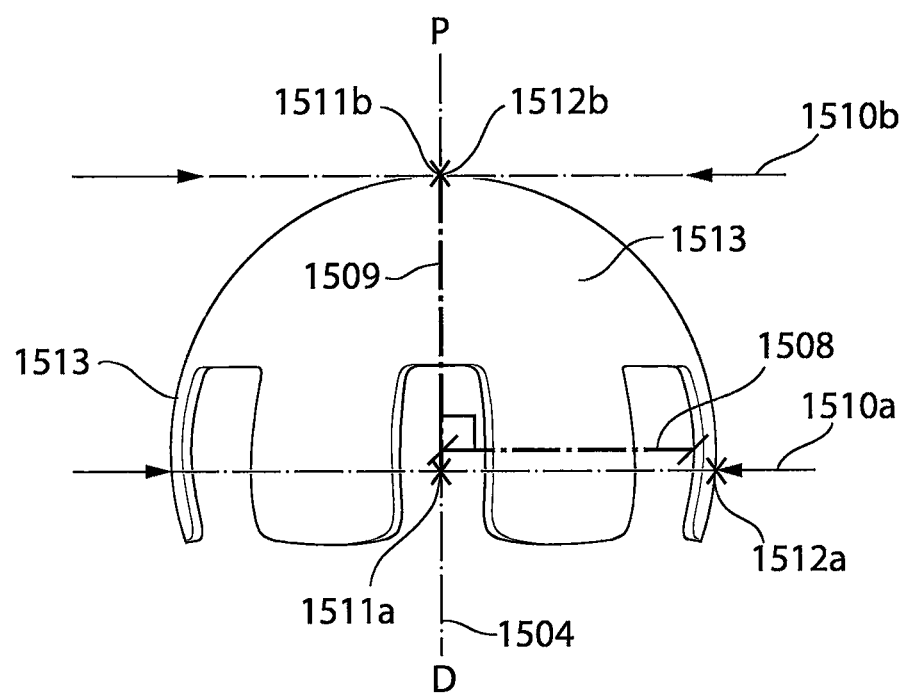
FIG. 5 shows the medical device according to one embodiment.

FIG. 5 shows the medical device according to one embodiment in which a maximum inner distance 1508 is extending from one or more predefined points selected along a lengthwise extending part 1509 of the medical device caput center axis 1504, in which said lengthwise extending part 1509 is defined by two cross-sections 1510a, 1510b of said artificial caput femur surface 45, extending perpendicular to the medical device caput center axis 1504, from both the distal 1511a and proximal 1511b end points of said part 1509 of the medical device caput center axis 1504, in which both cross-sections 1510a, 1510b are placed at the outer limit 1512a, 1512b of the weight carrying surface 1513 of the artificial caput femur surface, in proximal P and distal D direction, respectively. The part 1509 of the medical device caput center axis 1504 is placed between the cross-sections 1510a, 1510b.

Figure 6:
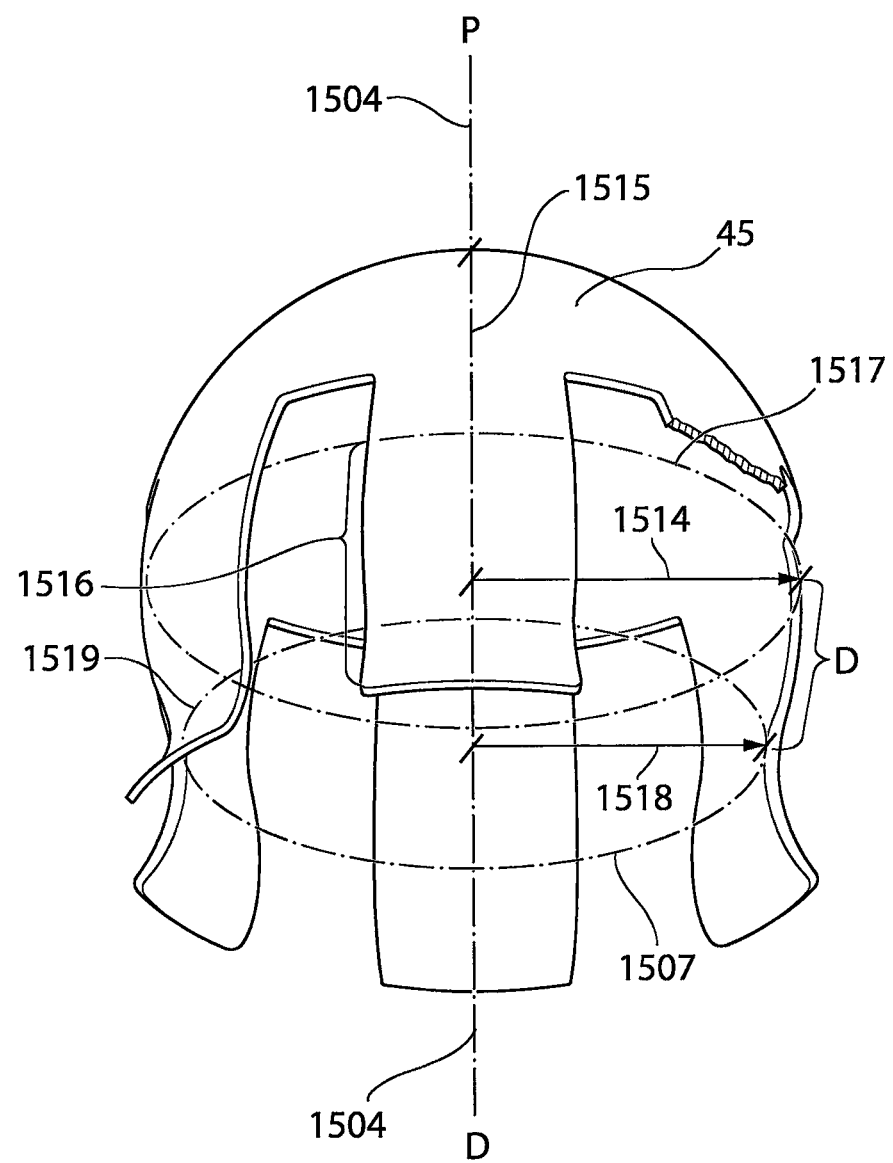
FIG. 6 shows the medical device according to another embodiment.

FIG. 6 shows the medical device according to an embodiment where the medical device has a maximum outer distance 1514 extending perpendicularly from a medical device caput center axis 1514 to the outer surface of the artificial caput femur surface. The artificial caput femur surface 45 comprises at least one first beyond part 1516 extending distally D, at least partly beyond a circular line 1517 of the maximum outer distance on the artificial caput femur surface 45, when implanted in said hip joint. The at least one first beyond part 1516 is adapted to have a closest distance 1518 from the inner surface of the first beyond part 1518 to the medical device caput center axis 1504, perpendicular to the medical device caput center axis 1504, being smaller than a maximum inner distance 1514 from the inner surface of the artificial caput femur surface 45 to the medical device caput center axis 1504, substantially perpendicular to the medical device caput center axis 1504. A maximum inner distance 1514 is extending from the medical device caput center axis 1504 substantially more proximal P than a major opening 1507. A lengthwise extending part of the medical device caput center axis 1504 is placed more proximal P than the major opening 1507, when the artificial caput femur surface 45 is mounted in a functional position in the hip joint. A circular line 1519 is defining the major opening, which could further be defined as the smallest opening through which the caput femur can pass.

The area of the at least one first beyond part 1516 extending a distance D beyond the maximum diameter of the caput femur 5, is here adapted to hold a locking member in place. The locking member could be a cord or wire, and can be placed around the artificial caput femur surface 45 for further fixation of the medical device. The band, cord or wire can be mechanically connected using a self locking member for forming a ring-shaped element able to assist in the fixation of the artificial caput femur surface 45 to the caput femur 5.

The distance D from the circular line 1517 of the maximum outer distance on the artificial caput femur surface 45 to the circular line 1519 is defining the major opening of the medical device. The distance D is chosen to extend to the circular line 1519 which have a closest distance 1518 from the inner surface of the first beyond part 1518 to the medical device caput center axis 1504. When the at least one first beyond part 1516 is extending to the circular line 1519 the articulation or motion range of the hip joint is not limitied. According to the embodiment shown in FIG. 6, the distance D is approximately 5 mm, however in other embodiments, the distance is approximately 10 mm.

FIG. 7 shows an artificial caput femur surface 45 in section having a major opening 52 adapted to travel over and beyond the maximum diameter of the caput femur 5. The maximum diameter of the caput femur 5 is according to this embodiment positioned at a corresponding largest diameter 61 of the artificial caput femur surface. A second distance 62 is the distance that the artificial caput femur surface 45 travels beyond the maximum diameter of the caput femur 5. Said distance 62 is the beyond part of the artificial caput femur surface 45 and is a part that enabled the mechanical fixation of the artificial caput femur surface 45 to the caput femur 5, by said beyond part of the medical device exerting a squeezing force of the caput femur 5 and/or collum femur and clasps the caput femur 5.

FIG. 8a shows an artificial caput femur surface 45 according to one embodiment in which the artificial caput femur surface 45 is adapted to pass beyond the maximum diameter of the caput femur 5. This enables a mechanical fixation using the form of said artificial caput femur surface 45. In this embodiment the artificial caput femur surface 45 comprises at least one slit 49 adapted to make said artificial caput femur surface 45 flexible for traveling over and beyond the maximum diameter of the caput femur 5. It is also conceivable that the artificial caput femur surface 45 comprises two or more artificial caput femur surface arms 50 which create a largest diameter 52. This largest diameter 52 is according to one embodiment smaller the maximum diameter of the caput femur 5 enabling the mechanical fixation of the artificial caput femur surface 45 by means of said artificial caput femur surface arms 50. For further fixation, a locking member 59, which could be a cord or wire 59, can be placed around the artificial caput femur surface 45 beyond the maximum diameter of the caput femur 5. The band, cord or wire 59 can be mechanically connected using an engagement member 60 for forming a loop-shaped element able to assist in the fixation of the artificial caput femur surface 45 to the caput femur 5.

FIG. 8b shows the artificial caput femur surface 45 when fixated to the caput femur 5 with the supporting band, cord or wire 59, as shown in FIG. 8a, placed around the artificial caput femur surface 45 beyond the maximum diameter of the caput femur 5. The arms 50 may also be adapted to go into the bone of caput femur 5 to lock said artificial caput femur surface 45.

Figure 8C:
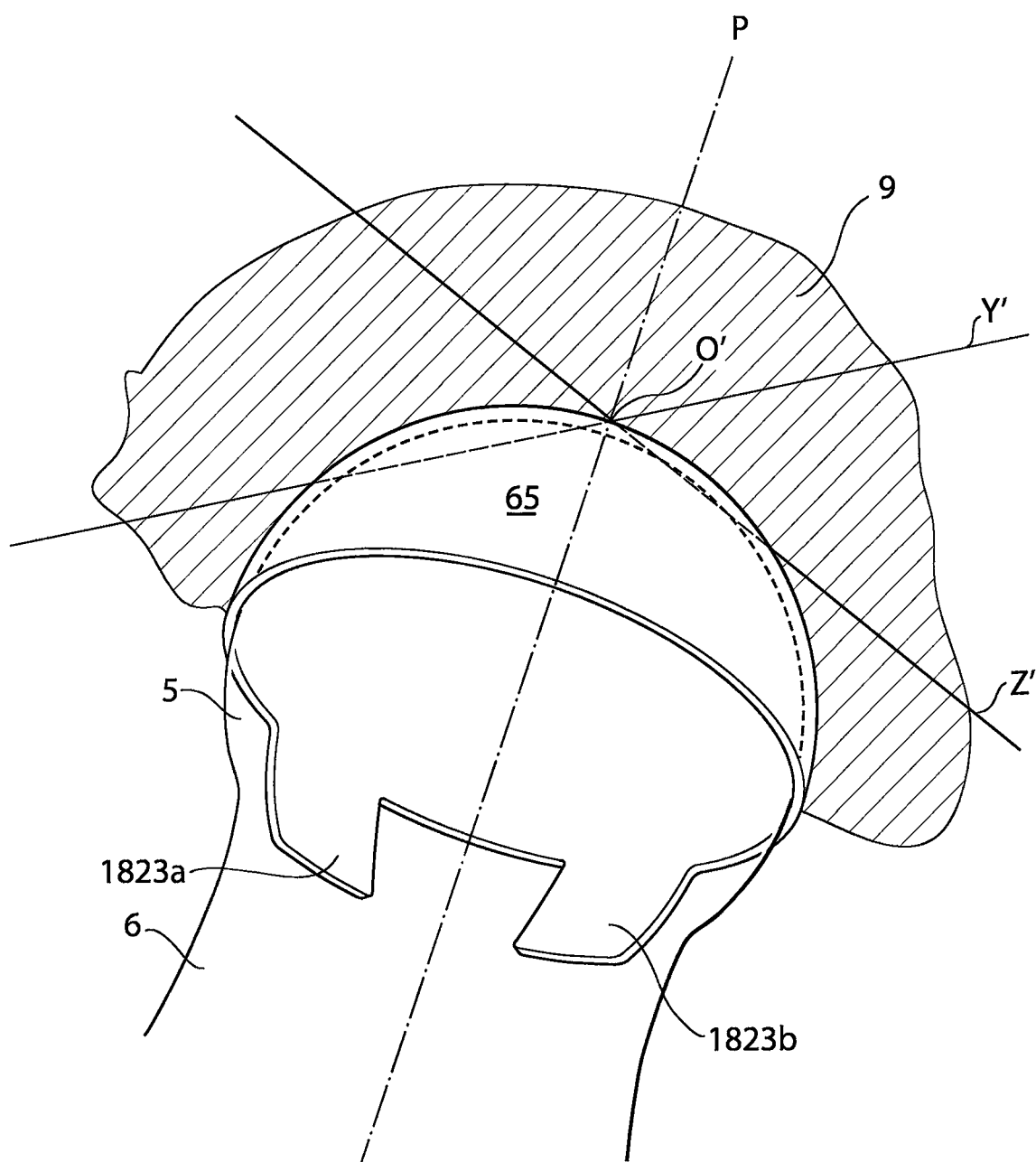
FIG. 8c shows the hip joint is section when a medical device is implanted.

FIG. 8c shows the hip joint in section when a medical device has been implanted. The two extending portions 1823a and 1823b extending distally and clasping the spherical portion of the caput femur 5. The hip joint has a caput femur 5 integrated with a collum femur 6 having a center axis P extending longitudinal along the collum and caput femur in the center thereof.

FIG. 9 shows an artificial caput femur surface 45 according to an embodiment in which the artificial caput femur surface comprises multiple movable portions 1224 connected to an interconnecting part 56 by operable joints 1205 placed along one side of the movable portions 1224. The artificial caput femur surface is further fixated to the caput femur by a band, cord or wire 59 placed beyond the maximum diameter of the caput femur 5 at a distance D from the maximum diameter and the most distal end of the moveable partitions 1224 directed away from the joints 1205. The artificial caput femur surface is fixated to the caput femur after the movable portions 1224 have been placed in there functional position clasping the caput femur 5, and be movable during an operation. The section A-A shows a movable portion 1224 when not in its functional state. The movable portion 1224 being connected to an interconnecting part 56 through a movable member in form of a hinge 1205 allowing the movable portion to move for being able to clasp the caput femur 5 and/or changing the maximum diameter of the artificial caput femur surface for passing through a hole smaller than the maximum diameter of the caput femur surface in its functional state, in which case the movable member is moved in a direction towards the center of the artificial caput femur surface (not shown).

Figure 10A:
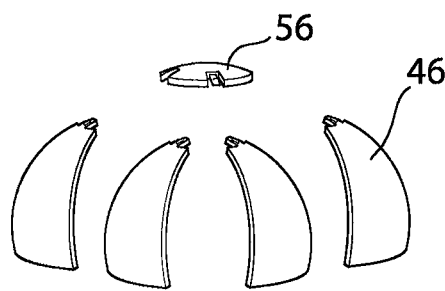
FIG. 10a-c shows an artificial acetabulum surface according to a second embodiment, FIG. 11a discloses the adjustable locking member to be mounted on the artificial acetabulum surface.
Figure 10B:
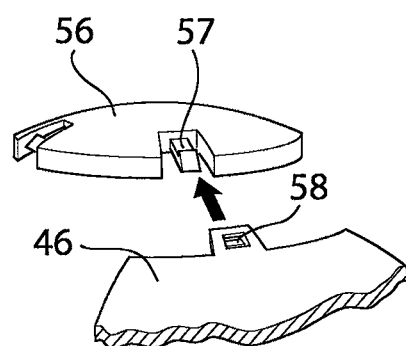
Figure 10C:
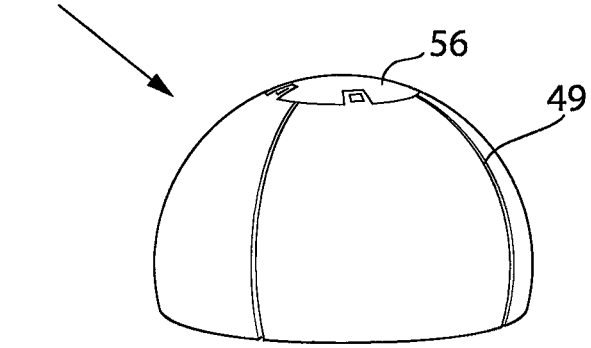

FIG. 10a-c shows an artificial caput femur surface 45 according to an embodiment in which the artificial caput femur surface comprises multiple portions 46 connected to an interconnecting part 56 by fastening means 57, 58 placed along one side of the portions 56. The fastening means comprises a first protruding portion 58 with an opening arranged on the one end of the portion 46. The opening in the first protruding portion 58 is adapted to interconnect with a second protruding portion 57 extending from a cut-out in the interconnection part 56. The multiple portions and the interconnection part can pass through a hole smaller than the maximum diameter of the caput femur surface and can be assembled to clasp the caput femur 5 after being inserted in the hip joint.

Figure 11A:
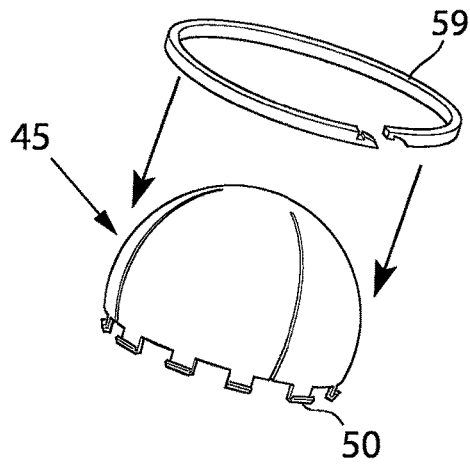
FIG. 11b-11e shows different embodiments of a locking member and an engagement member.

FIG. 11a discloses the adjustable locking member 59 to be mounted on the artificial caput femur surface 45. The locking member 59 is a loop-shaped element having two ends 59a, 59b adapted to be mechanically connected using an engagement member 60, thus forming a closed loop with a certain circumference. The locking member 59 can be made out of an elastic material which deforms under stress (e.g. external forces), but returns to its original shape when the stress is removed.

The artificial caput femur surface 45 comprises two or more artificial caput femur surface arms 50 which create a largest diameter 52. To lock the artificial caput femur to the caput femur 5, the locking member 59 is, when it is in an open state, pulled over the surface 45 until it at least reaches an area extending a distance D beyond the maximum diameter of the caput femur 5. The locking member 59 can also be pulled until it reaches and rests on surface arms 50. When in its final position, the locking member ends 59a, 59b are mechanically connected by the engagement member 60, and the artificial caput femur is held in place.

FIG. 11b-11e shows different embodiments of the locking member 59 and the engagement member 60.

Figure 11B:
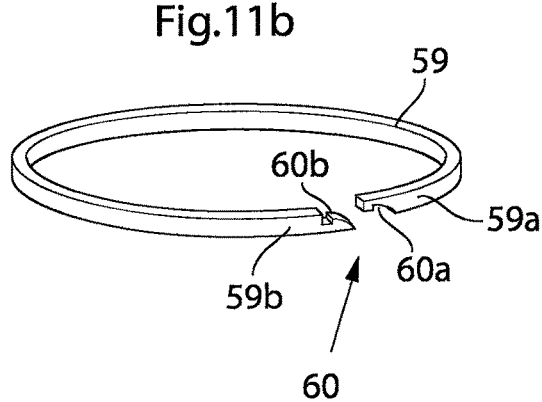

A first embodiment of a locking member 59 with engagement member 60 is disclosed in FIG. 11b. The engagement member 60 comprises a first and a second part 60a, 60b arranged in the first and second locking member end 59a, 59b, respectively. The first and second engagement member parts 60a, 60b have the shape of protrusions extending axially from the first and second locking member end, upwards and downward respectively. Thus forming a horizontally arranged gripping claw. The first engagement member part 60a has a cut-out in its lower surface and the second engagement member part 60b has a cut-out in its upper surface. The cut-outs are so arranged that they form an upper and a lower hook adapted to mechanically self connect by using the elasticity of the material and thus to form a loop with a certain circumference adapted to the diameter of the caput femur 5.

Figure 11C:
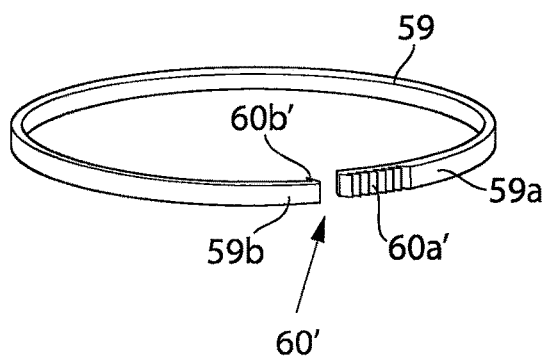

In a second embodiment of the locking member 59, shown in FIG. 11c, the engagement member 60' is arranged in one first and second end 59a, 59b of the locking member. In the first locking member end 59a one first engagement member part 60a' in the form of a protrusion extending radially, towards the center of the loop is arranged. The first engagement member part 60a is adapted to engage with one corresponding second engagement member part 60b which is a protrusion arranged in the other second end 59b of the locking member extending radially, from the center of the loop. The protrusions together are forming an engagement member in the form of a vertically arranged gripping claw 60'. The circumference of the locking member can be adjusted by using more than one second engagement member parts 60b and arranging them at different distances from the second end 59b of the locking member. In the second embodiment in FIG. 11c there are more than one, preferably between three and six, gripping claws 60b' arranged on the second end 59b of the locking member 59. The locking member 59 diameter can thus be adjusted.

Figure 11D:
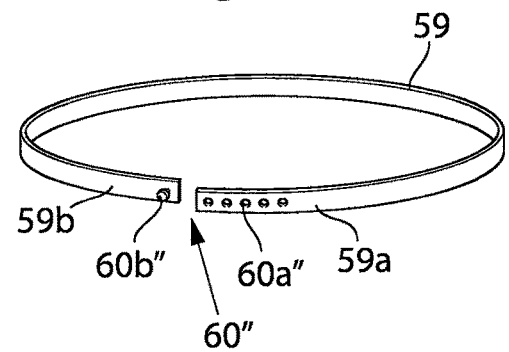

A third embodiment of the locking member 59 is disclosed in FIG. 11d. In one first end 59a of the locking member 59 there is a first engagement member part 60a" in the form of a protrusion adapted to fit into a corresponding second engagement member part 60a" in the form of a recess or a hole in the other second end 59b of the locking member 59. It is also possible to have more than one hole so that the circumference of the locking member 59 is adjustable.

Figure 11E:
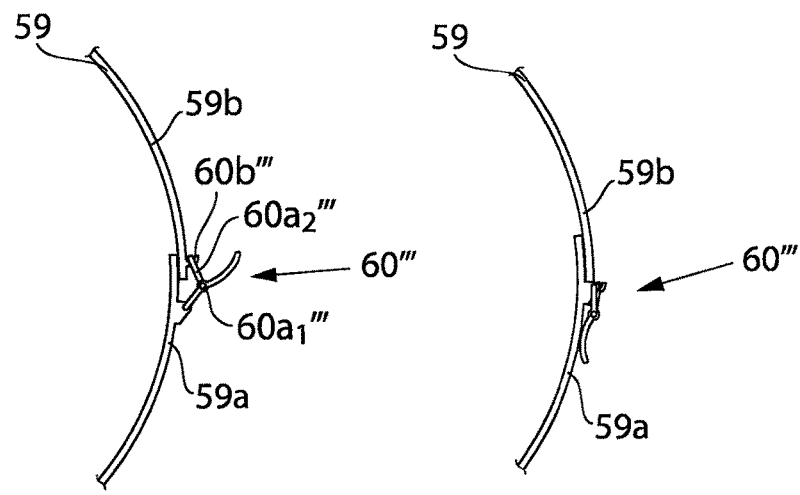

A forth embodiment of the locking member 59 is disclosed in FIG. 11e. Here the first and second ends 59a, 59b of the locking member 59 are connected by using an engagement member 60''' comprising two pivotable first locking parts 60a1''', 60a2''' and one second locking part 60b'''. The first locking part 60a1''' is pivotably attached both to the first end 59a of the locking member 59 and to the second locking part 60a2'''. The second locking part 60a2''' is attached to the first locking part 60a1''' in an engagement point arranged between the outer ends of the first locking part 60a1''', preferably in a point arranged substantially in the middle of the first locking part 60a1'''. The second locking part 60a2''' is also adapted to engage with a protruding part 60b''' arranged in the second end 59b of the locking member 59. When the second locking part 60a2''' is engaged with the protruding part 60b''', the first and second end of the locking member 59a, 59b is locked together forming a closed loop with a first circumference. The first and second locking member ends 59a, 59b can be pulled together forming a closed loop with a second circumference firmly enclosing the artificial caput femur and locking it to the caput femur 5. The first and second locking member ends 59a, 59b are pulled together by pivoting the first locking part around its engagement point in the first end 59a of the locking member. The first and second locking member ends 59a, 59b can be arranged either overlapping each other or being arranged end to end when locked together, thus forming a loop with the second circumference.

Figure 12A:
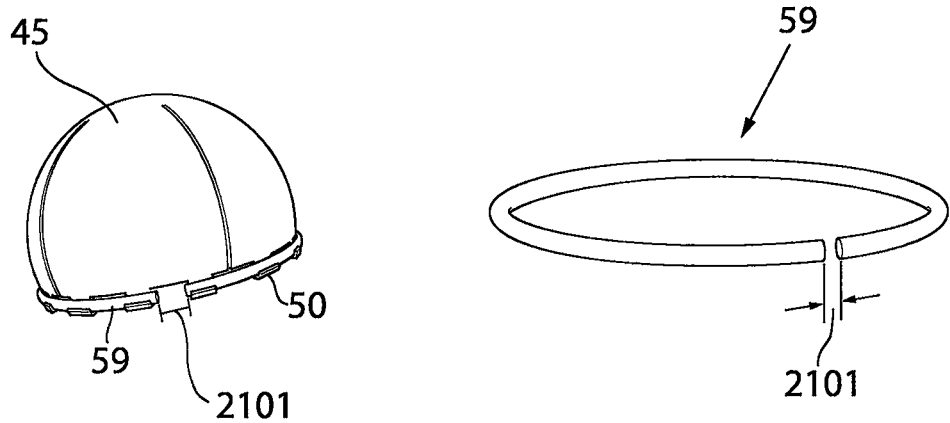
FIG. 12a shows a medical device and a locking member according to yet another embodiment.

FIG. 12a shows yet another embodiment of the locking member, in which the locking member does not encircle the caput femur surface 45 completely, thus leaving a distance 2101 in which there is no locking member. According to the embodiment shown in FIG. 12a the locking member 59 clamps the artificial caput femur surface by the locking member being made from an elastic material, such as stainless steel. The construction with locking member enables the artificial caput femur surface to be made from a more resilient material, for allowing the artificial caput femur surface to pass over the larger parts of the caput femur. One advantage with the embodiment shown in FIG. 12 is that the locking member 59 does not have to be as elastic as the locking members that totally encircles the caput femur, to still be mountable by the surgeon in situ.

Figure 12B:
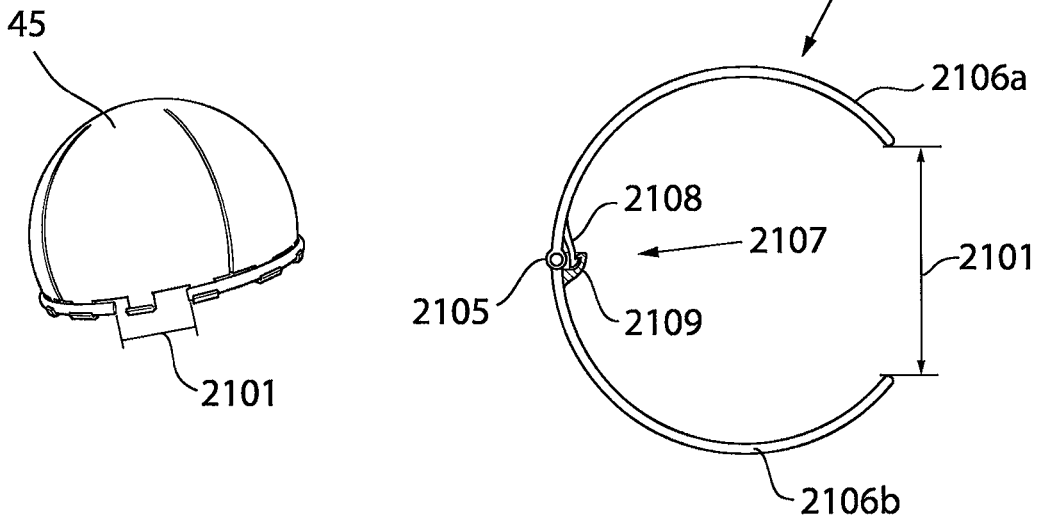
FIG. 12b shows a medical device and a locking member according to yet another embodiment.

FIG. 12b shows a locking member according to an embodiment similar to the embodiment described previously, with reference to FIG. 12a. However, according to the embodiment shown in FIG. 12b, the locking member 59 comprises a hinge 2105 placed at the center of the locking member 59 to which two portions 2106a, 2106b of the locking member are connected. In connection to the hinge a locking device is placed comprising an male 2108 part adapted to connect to a female part 2109, thus creating a locking position. The locking member in the locking position clasps the artificial caput femur surface 45 and thus further fixates the artificial caput femur surface 45 to the caput femur. The embodiment of FIG. 12b, with the hinge, enables the locking member to be made from a less elastic material than is necessary in embodiments where the entire locking member is made from a single piece of material (such as the embodiment described with reference to FIG. 12a). The embodiment could further reduce the force needed to mount the locking member 59 onto the artificial caput femur 45 in situ.

FIG. 13a shows a locking member 59 according to yet another embodiment, in which the locking member 59 comprises a first and second unit 2102a, 2102b placed at two sides of a slit 49 in the artificial caput femur surface 45. The first unit 2102a comprises a male part 2103 which is insertable into a female part 2104 of the second unit 2102b, in which it locks and thus places the slit 49 in a more closed state for fixating the artificial caput femur 45 surface to the caput femur.

FIG. 13b shows the medical device according to an embodiment in which the locking member 59 is placed centrally in the top of an embodiment of the artificial caput femur surface 45, in which the artificial caput femur surface is dividable into two halves. The locking member comprises, in accordance with the embodiment shown with reference to FIG. 13a, a first and second unit 2102a, 2102b, wherein said first unit comprises a male part 2103 adapted to lock inside of a female part housed in the second unit.

FIG. 14 shows an embodiment of the locking member 59 in which the locking member 59 is adapted to travel from a first point of the artificial caput femur surface 45 through the bone of caput and/or collum femur and to a second point of the artificial caput femur surface 45. This embodiment could enable the locking member to fixate the artificial caput femur surface 45 to the caput femur by exerting a squeezing force and thus clamping the caput femur, and/or by the locking member 59 being inside the bone actually creating a mechanical lock thereby. According to the embodiment shown in FIG. 14 the locking member 59 goes from one point of the artificial caput femur surface 45 to another point on the artificial caput femur surface 45, through the bone of the caput/collum femur. However in other embodiments (not shown) the locking member goes from a point of the artificial caput femur surface and into the bone of caput/collum femur, in these embodiments the locking members could be mechanical fixating members, such as orthopedic screws.

Figure 15:
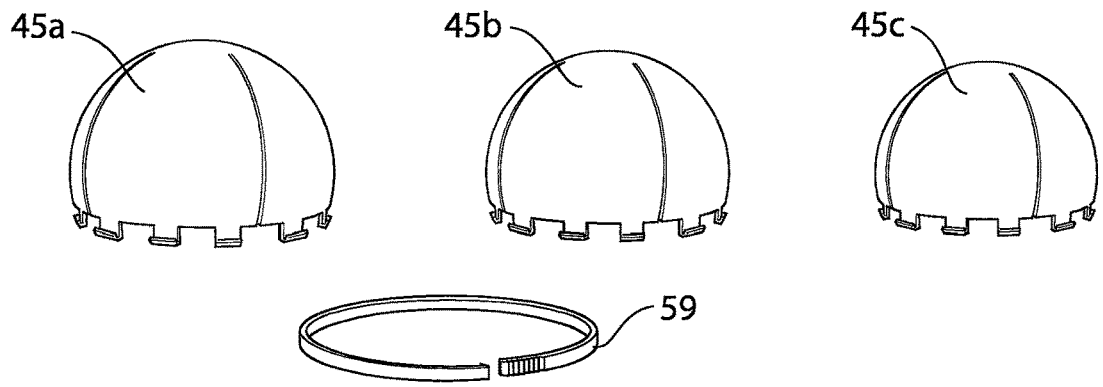
FIG. 15 shows a first kit comprising three artificial caput femur surfaces and one locking member.

FIG. 15 shows a kit according to a first embodiment in which the kit comprises three different sizes of artificial caput femur surfaces 45a,b,c, which could be chosen on the basis of the particular patient, an a locking member 59 with several states which thus could be tightened around the different artificial caput femur surfaces 45a,b,c to fit the particular patient.

Figure 16:
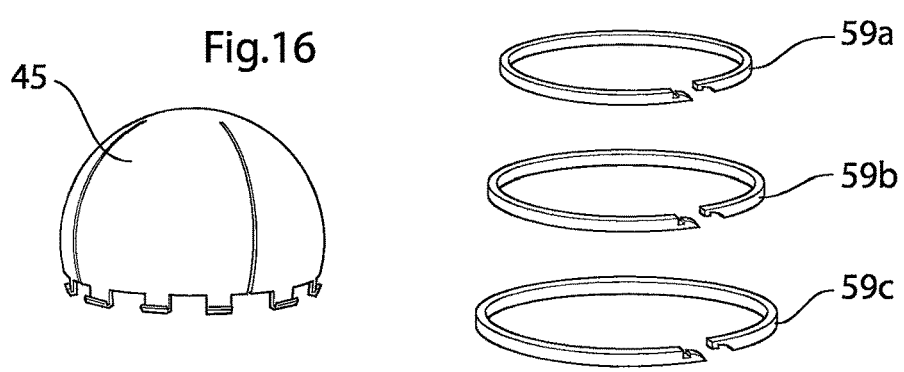
FIG. 16 shows a second kit comprising one artificial caput femur surfaces and three locking members.

FIG. 16 shows a kit according to a second embodiment in which the kit comprises one artificial caput femur surface 45 and three different sizes locking member 59*a,b,c* which thus can be placed encircling the artificial caput femur surface 45 and be chosen for the particular femoral bone of a particular patient.

Figure 17:
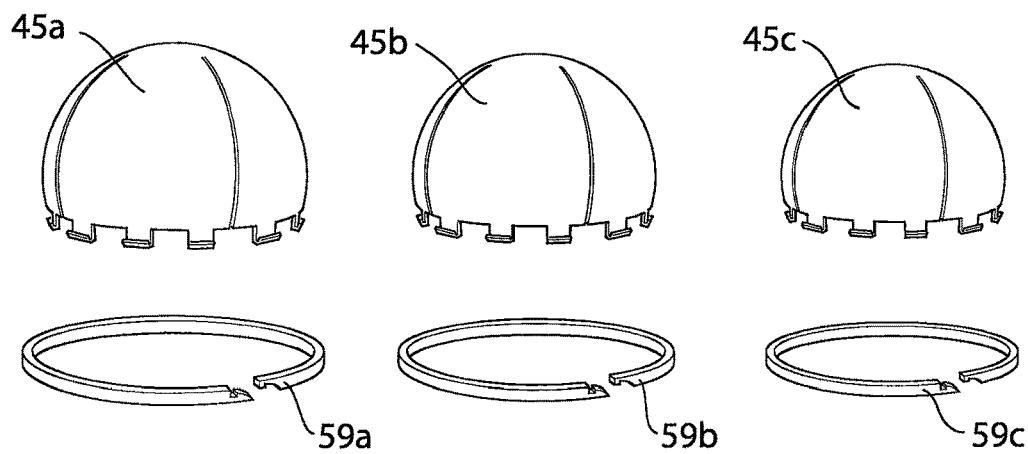
FIG. 17 shows a third kit comprising three artificial caput femur surfaces and three locking members.

FIG. 17 shows a kit according to a second embodiment in which the kit comprises three different sizes of artificial caput femur surfaces 45*a,b,c*, which could be chosen on the basis of the particular patient, and three different sizes of locking members 59*a,b,c* which thus can be placed encircling the artificial caput femur surface 45 and be chosen for the particular femoral bone of a particular patient.

The kit solutions enables the orthopedic surgeon to choose a suitable medical device when the caput femur is exposed, since determining the exact size and shape of the caput femur is very hard from merely images created from outside of the body.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

Please note that any embodiment or part of embodiment as well as any method or part of method could be combined in any way. All examples herein should be seen as part of the general description and therefore possible to combine in any way in general terms.

The invention claimed is:

1. A method for implantation of a locking member in a hip joint of a patient, the hip joint having a caput femur integrated with a collum femur having a center axis extending longitudinal along the collum and caput femur in the center thereof, the method comprise the following steps;

performing an operation in a hip joint surgically or arthroscopically, placing an artificial hollow caput femur surface mounted onto caput femur, placing a locking member for assisting in the fixation of the artificial caput femur surface, wherein said artificial caput femur surface comprises at least one extending portion adapted to clasp a portion of the caput and/or collum femur, and wherein the locking member is adapted to be placed onto the artificial caput femur surface at the extending portion, clasping with the least one extending portion a portion of the caput and/or collum femur, and wherein said locking member comprises an element adapted to lock said artificial caput femur surface such that the caput femur remains clasped and restrained in said artificial caput femur surface locking by said locking member element said artificial caput femur surface such that the caput femur is remaining clasped and restrained in said artificial caput femur surface.

2. The method according to claim 1, wherein said locking member is adapted to lock in at least a first and a second locking position, the method comprising the steps of;

locking in said first locking position, and locking in second position locking tighter the artificial caput femur surface with at least one extending portion, to the caput and/or collum femur.

3. The method according to claim 1, wherein said locking member is adapted to lock in at least a first and a second locking position, the method comprising the steps of;

locking in said first locking position a first artificial hollow caput femur surface, and locking in second position a second smaller artificial caput femur surface with at least one extending portion, to the caput and/or collum femur.

4. The method according to claim 1 using a locking member comprising a loop-shaped element, the method comprise the step of; locking in situ said loop shape surrounding the caput and/or collum femur.

5. The method according to claim 4, locking said loop shaped element in a first locking state, in which said loop shape has a first inner circumference, and locking said loop shaped element in a second locking state, in which said loop shaped element has a second smaller inner circumference.

6. The method according to claim 1, wherein said locking member further comprises a medical device comprising, an artificial caput femur surface being hollow, having a major opening adapted to be directed distally and being adapted to replace a caput femur hip joint surface, wherein said artificial caput femur surface further having;

a medical device caput center axis passing through said major opening, being aligned with the caput and collum femur center axis, when said medical device is implanted in a functional position in the hip joint, wherein said medical device comprises a central part and a surrounding part, the central part being aligned with the medical device center axis and the surrounding part surrounding the surface of the caput femur not including the central part, and wherein said medical device further comprises;

an inner surface adapted to have a first distal distance extending perpendicularly from said medical device caput center axis to said inner surface of said surrounding part of said artificial caput femur surface, said first distal distance being shorter than a second proximal distance extending perpendicularly from said medical device caput center axis to said inner surface of said artificial caput femur surface, said second proximal distance extending from a more proximal position on said medical device caput center axis than said first distal distance, being the second proximal distance, when said artificial caput femur surface is implanted in said functional position in the hip joint, the artificial caput femur surface comprise a lock holding member for holding the locking member in its position, the method involves the step of;
   placing the artifical caput femur surface onto caput femur during a surgical or arthroscopical operation, a
   placing the locking member and
   locking said artifical caput femur surface to caput femur,
   holding said locking member in place by said lock holding member.

7. A method for implantation at least one medical device in a hip joint of a patient, the hip joint having a caput femur integrated with a collum femur having a center axis extending longitudinal along the collum and caput femur in the center thereof, wherein the collum femur is placed more distal than caput femur, wherein;
   said medical device system comprises two or more medical devices, wherein each of the medical devices comprising:
      an artificial caput femur surfaces being hollow, having a major opening adapted to be directed distally, when said medical device is implanted, wherein said artificial caput femur surface is adapted to replace a caput femur hip joint surface, further having;
      a medical device caput center axis passing through said major opening, being aligned with the caput femur center axis, when said medical device is implanted in a functional position in the hip joint, wherein said medical device comprises a central part and a surrounding part, the central part being aligned with the medical device center axis and the surrounding part surrounding the surface of the caput femur not including the central part, and wherein said medical device further comprises;
      an inner surface adapted to have a first distal distance extending perpendicularly from said medical device caput center axis to said inner surface of the surrounding part of said artificial caput femur surface, said first distal distance being shorter than a second proximal distance extending perpendicularly from said medical device caput center axis to said inner surface of said artificial caput femur surface, said second proximal distance extending from a more proximal position on said medical device caput center axis than said first distal distance, being the second proximal distance, when said artificial caput femur surface is implanted in said functional position in the hip joint, and
   a locking member for implantation in a hip joint of a patient, wherein said locking member is adapted to assist in the fixation of said medical device to the collum and/or caput femur, wherein said locking member comprises an element adapted to lock said artificial caput femur surface such that the caput femur remains clasped and restrained in said artificial caput femur surface, wherein at least one of said artificial caput femur surfaces has a size adapted to replace the caput femur hip joint surface of a corresponding size, wherein the method includes the step of;
   surgically or arthroscopically implanting two or more artificial caput femur surfaces to find the right size to lock onto the caput femur.

8. The method according to claim 7, further comprising two or more locking members, wherein the two locking members have different sizes, when in their locking position, and thus being adapted to lock different artificial caput femur surfaces of different sizes to a caput femur, or an artificial caput femur surfaces to caput femurs of different sizes, such that the caput femur remains clasped and restrained in the artificial caput femur surface, when locked by one of the two or more locking members having the matching size, the method involves the step of; using two or more locking members to lock the artificial caput femur surface of the correct size to the caput femur.

9. The method according to claim 1, wherein said at least one extending portion is mounted according to at least one of the following alternatives:
   a) extending circumferentially discontinuously along said equator line having enough circumferential distance lacking any extending portion and
   b) extending with different distal extension in different extending portions or part of such portion of said circumferential extension.

* * * * *